(12) United States Patent
Edwards et al.

(10) Patent No.: US 7,700,615 B2
(45) Date of Patent: Apr. 20, 2010

(54) CELL MIGRATION INHIBITING COMPOSITIONS AND METHODS AND COMPOSITIONS FOR TREATING CANCER

(75) Inventors: David L. Edwards, Scottsdale, AZ (US); Michael E. Berens, Gilbert, AZ (US); Christian Beaudry, Scottsdale, AZ (US)

(73) Assignee: Avolix Pharmaceuticals, Inc., Scottsdale, AZ (US)

( * ) Notice: Subject to any disclaimer, the term of this patent is extended or adjusted under 35 U.S.C. 154(b) by 822 days.

(21) Appl. No.: 11/345,132

(22) Filed: Feb. 1, 2006

(65) Prior Publication Data

US 2006/0128742 A1 Jun. 15, 2006

Related U.S. Application Data

(62) Division of application No. 10/161,843, filed on Jun. 4, 2002, now Pat. No. 7,012,100.

(51) Int. Cl.
*A61K 31/47* (2006.01)
*A61K 31/45* (2006.01)

(52) U.S. Cl. .................. 514/294; 514/741; 514/740; 514/751

(58) Field of Classification Search .................. 514/294, 514/741, 740, 751
See application file for complete search history.

(56) References Cited

U.S. PATENT DOCUMENTS

| | | | |
|---|---|---|---|
| 4,196,202 | A | 4/1980 | Okada |
| 4,906,457 | A | 3/1990 | Ryan |
| 4,929,635 | A | 5/1990 | Coquelet et al. |
| 5,189,212 | A | 2/1993 | Ruenitz |
| 5,556,992 | A | 9/1996 | Gaboury et al. |
| 5,773,460 | A | 6/1998 | Gaboury et al. |
| 5,856,517 | A | 1/1999 | Huryn et al. |
| 5,877,185 | A | 3/1999 | Kun et al. |
| 5,932,515 | A | 8/1999 | Rourke |
| 5,985,837 | A | 11/1999 | Ritter et al. |
| 5,998,160 | A | 12/1999 | Berens |
| 6,030,994 | A | 2/2000 | Huryn et al. |
| 6,054,468 | A | 4/2000 | Geerts et al. |
| 6,310,060 | B1 | 10/2001 | Barrett et al. |
| 6,335,163 | B1 | 1/2002 | Sharon |
| 6,359,013 | B1 | 3/2002 | Reddy et al. |
| 2001/0018422 | A1 | 8/2001 | Ritter et al. |
| 2002/0048813 | A1 | 4/2002 | Gertler et al. |

FOREIGN PATENT DOCUMENTS

| | | |
|---|---|---|
| EP | 0677292 | 10/1995 |
| EP | 0747389 | 12/1996 |
| GB | 2284153 | 5/1995 |
| GB | 2288333 | 10/1995 |
| GB | 2303790 | 3/1997 |
| GB | 2312375 | 10/1997 |
| WO | 91/07166 | 5/1991 |
| WO | 93/24442 | 12/1993 |
| WO | 96/07431 | 3/1996 |
| WO | 96/29067 | 9/1996 |
| WO | 97/46552 | 12/1997 |
| WO | 98/58639 | 12/1998 |
| WO | 99/01421 | 1/1999 |
| WO | 01/26708 | 8/2001 |
| WO | 01/85166 | 11/2001 |
| WO | 02/20462 | 3/2002 |

OTHER PUBLICATIONS

He et al., "Construction and Preliminary Screening of a Human Phage Single-Chain Antibody Library Associated with Gastric Cancer," Journal of Surgical Research, Feb. 2002, vol. 102, pp. 150-155.
Berens et al., "The role of extracellular matrix in human astrocytoma migration and proliferation studied in a microliter scale assay," Clin. Exp. Metastasis, 1994, vol. 12, pp. 405-415.
Kramer et al., "Melanoma Cell Adhesion to Basement Membrane Mediated by Integrin-related Complexes," Cancer Research, Jan. 1989, vol. 49, pp. 393-402.
International Search Report, PCT/US03/017399, mailed Nov. 17, 2005.
Mariani et al., "Glioma cell motility is associated with reduced transcription of proapoptotic and proliferation genes: a cDNA microarray analysis," 2001, Journal of Neuro-Oncology, vol. 53, pp. 161-176.
Foreign Office Action dated Jan. 28, 2008 for corresponding European patent application No. 03756370.7 (5 sheets).

*Primary Examiner*—Ardin Marschel
*Assistant Examiner*—Zohreh Vakili
(74) *Attorney, Agent, or Firm*—Fennemore Craig, P.C.

(57) ABSTRACT

Methods for treating an individual having cancer are provided. The method may include administering a cell migration inhibitor and a chemotherapeutic agent to the individual to inhibit migration of cancer cell. Inhibiting cell migration may increase cell division. In this manner, the cell migration inhibitor and the chemotherapeutic agent in combination may have increased efficacy compared to the chemotherapeutic agent alone due to the increased cell division. The cell migration inhibitor may include any of the inhibitors described herein. For example, the cell migration inhibitor may be an organic molecule having a molecular weight of less than about 700, a monoclonal antibody, or a natural product.

11 Claims, 17 Drawing Sheets

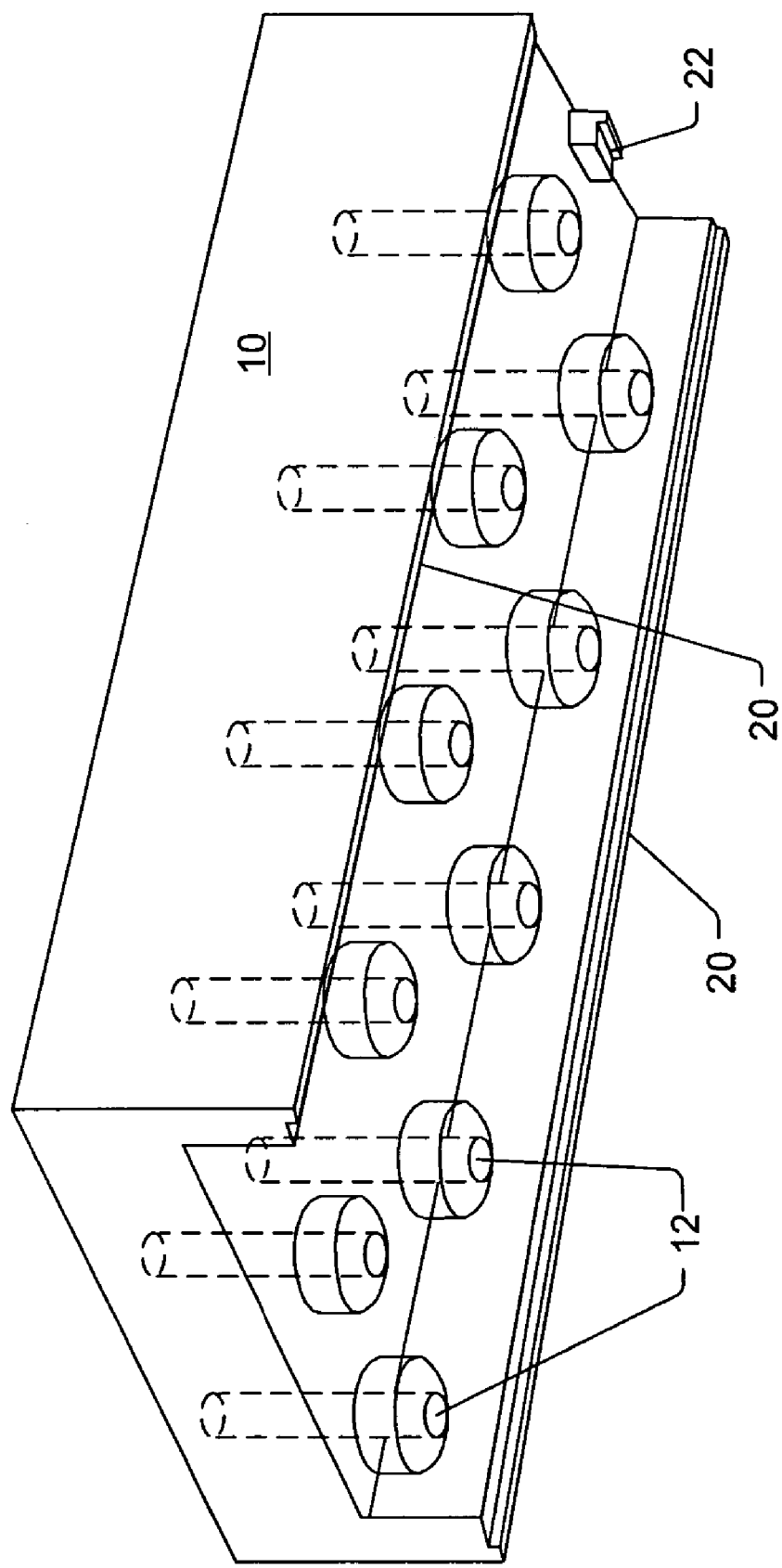

CELL MIGRATION INHIBITING COMPOSITIONS AND METHODS AND COMPOSITIONS FOR TREATING CANCER

CONTINUING DATA

This application is a divisional application of Ser. No. 10/161,843 filed Jun. 4, 2002, now U.S. Pat. No. 7,012,100.

BACKGROUND OF THE INVENTION

1. Field of the Invention

This invention generally relates to cell migration inhibiting compositions and method and compositions for treating cancer. Certain embodiments relate to methods for identifying compositions that inhibit cell migration and methods for identifying compositions that have synergy with a chemotherapeutic agent.

2. Description of the Related Art

Abnormalities in how living cells move are the underlying cause of many human diseases. Cancer, heart disease, arteriosclerosis, wound healing, arthritis, and some autoimmune diseases all share common elements in that cell movement is perturbed. This change may be either accelerated or deficient cell movement.

Of the diseases caused by abnormal cell movement, cancer is the second leading cause of death in the United States. There have been approximately 16 million cancer cases diagnosed since 1990, and 5 million lives have been lost to cancer. 1 in 4 people in the United States will die of cancer. The American Cancer Society projects that 1,220,100 new cancer cases will be diagnosed in 2002 and that 552,200 Americans will die of cancer or more than 1500 people a day. These estimates exclude non-invasive cancers and do not include basal cell and squamous cell cancers. In fact, skin cancers are more common than cancers of any other organ, and over 1.3 million cases of basal cell and squamous cell skin cancer are expected to be diagnosed this year. The financial cost of cancer in the United States exceeds $100 billion per year.

Although the critical role of cell migration (invasion and metastasis) in cancer is recognized, the absence of technology for screening chemicals for effects on cell migration has left cell migration largely unexplored. Example of methods for studying cell migration include, for example, the Boyden Chamber Assay and the Scratch Wound Assay. The Boyden Chamber Assay generally involves placing cells on one side of a membrane. The membrane has pores of a diameter smaller than the diameter of the cells under investigation. After the cells are placed on one side of the membrane, the chamber is incubated for a period of time. Cell migration may be assessed by determining the number of cells that are present on the other side of the membrane after the period of time. The Scratch Wound Assay generally involves scraping a confluent monolayer of cells thereby creating a "wound" in the monolayer. Cell migration may be assessed by monitoring filling of the wound by surrounding cells. Another migration assay is commercially available from Chemicon International, Inc., Temecula, Calif. This assay generally involves dissociating migratory cells on the bottom of an insert membrane. The dissociated cells are lysed and detected using a dye that exhibits fluorescence when bound to cellular nucleic acids.

There are, however, several disadvantages to the above methods for studying cell migration. For example, these methods for studying cell migration are cumbersome, expensive, require relatively large amounts of reagents, insensitive, and are difficult to reproduce.

SUMMARY OF THE INVENTION

An embodiment of the invention relates to a method for identifying a chemical that inhibits cell migration. In an embodiment, the method may include depositing the cancer cells on a substrate at a predetermined location and treating the cancer cells with the chemical on the substrate. For example, the method may include depositing the cancer cells using guided cell sedimentation and treating the cancer cells with the chemical subsequent to the sedimentation. The method may include measuring a cell migration rate of cancer cells treated with a chemical selected from a library of chemicals and a cell migration rate of untreated cancer cells. The library of chemicals may include organic molecules having a molecular weight of less than about 700. In addition, all of the chemicals in the library may include organic molecules. In alternative embodiments, the library of chemicals may include monoclonal antibodies and/or natural products. Measuring the cell migration rate may include measuring a distance that the cancer cells migrate radially from an approximate center of a sample of cancer cells. In one embodiment, the method may also include measuring an additional property of the cancer cells treated with the chemical and the cancer cells in the untreated control sample.

If the treated cancer cells have a lower cell migration rate than the untreated cancer cells, the method may include measuring a cell migration rate of cancer cells treated with different dosages of the chemical. The method may also include identifying the chemical as a cell migration rate inhibiting chemical if the cell migration rate decreases as the dosage increases. In another embodiment, the method may also include determining if a combination of the chemical and a chemotherapeutic agent exhibits synergistic killing of the cancer cells.

In an additional embodiment, the method may include measuring a cell migration rate of a plurality of samples of the cancer cells treated with different chemicals selected from the library. Such a method may also include selecting one or more of the chemicals having cell migration rates lower than a cell migration rate of at least the untreated control sample. In addition, the method may include measuring a cell migration rate of cancer cells treated with different dosages of the selected chemicals. The method may further include identifying one or more of the selected chemicals as cell migration inhibiting chemicals if the cell migration rate of the cancer cells treated with different dosages of the selected chemicals decreases as the dosage increases.

An additional embodiment relates to a method for identifying a chemical that alters cell migration. The method may include measuring the cell migration rate of the cells treated with the chemical and the cell migration rate of untreated cells. If the treated cells have a different cell migration rate than the untreated cells, the method may include measuring the cell migration rate of cells treated with different dosages of the chemical. The method may also include identifying the chemical as a cell migration altering chemical if the cell migration rate varies depending upon the dosage.

An embodiment of a method for inhibiting cell migration may include treating cells with a cell migration inhibitor having a general formula of:

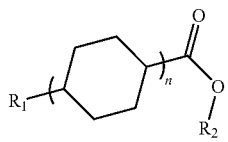

The chemical may be an organic molecule having a molecular weight of less than about 700. In the above general formula, n may be 1 or 2. $R_1$ may be selected from the group consisting of methyl, propyl, butyl, pentyl, hexyl, tert-butyl, acetoxy, phenyl, biphenyl-4-yl, 4-iodo-phenyl, and 4-pentyl-phenoxycarboynylmethyl. $R_2$ may be selected from the group consisting of hydrogen, 4-acetyl-amino, 4-(2-cyano-ethyl)-phenyl, 4-propenyl-phenyl, 4-pentyl-phenyl, 4-bromo-phenyl, 4-chloro-phenyl, 3-chloro-4-fluoro-phenyl, 4-acetyl-phenyl, 4-hydroxy-phenyl, 4-ethoxy-phenyl, 4-oxtyloxy-phenyl, 2,3-dicyano-4-hexyloxy-phenyl, 4-butoxy-2,3-dichloro-phenyl, 4-pentanoyl-phenyl, 4-cyano-phenyl, biphenyl-4-yl, 4'-methyl-biphenyl-4-yl, 4'-cyano-biphenyl-4-yl, 2-(4-bromo-phenyl)-2-oxo-ethyl, 2-(4'-bromo-biphenyl-4-yl)-2-oxo-ethyl, 4-cyclohexanecarbonyloxy-phenyl, and 4-benzoic acid ethyl ester. One embodiment of the chemical that exhibited cell migration inhibition is 4'-propyl-bicyclohexyl-4-carboxylic acid.

An additional embodiment of a method for inhibiting cell migration may include treating cells with a cell migration inhibitor having a general formula of:

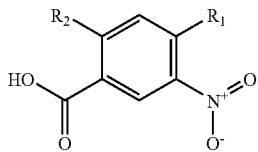

This chemical may also be organic molecule having a molecular weight of less than about 700. $R_1$ is selected from the group consisting of hydrogen, methyl, methoxy, bromo, amino, 2-hydroxy-ethylamino, and 3-hydroxy-propylamino. $R_2$ is selected from the group consisting of hydrogen and acetylamino. In one embodiment, $R_1$ or $R_2$ may be hydrogen. In another embodiment, $R_1$ and $R_2$ may be acyclic groups. In an additional embodiment, $R_1$ and $R_2$ may not be nitro groups. One embodiment of the chemical that exhibited cell migration inhibition is 4-methyl-3-nitro-benzoic acid.

Another embodiment of a method for inhibiting cell migration may include treating cells with a cell migration inhibitor having a general formula of:

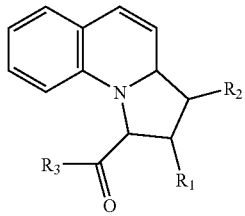

which may be an organic molecule having a molecular weight of less than about 700. $R_1$ may be selected from the group consisting of phenyl, 3,4-dimethoxy-phenyl, benzo[1,3]dioxol-5-yl, 4-fluoro-phenyl, and 4-methoxy-phenyl. $R_2$ may be selected from the group consisting of 4-(2,2-dicyano-1-cyclopropyl-vinyl) and dicyano. $R_3$ may be selected from the group consisting of 4-chlorophenyl, phenyl, and cyclopropyl. One embodiment of the chemical that exhibited cell migration inhibition is 1-(4-chloro-benzoyl)-2-(3,4-dimethoxy-phenyl)-1,2-dihydro-3aH-pyrrolo[1,2-a]quinoline-3,3-dicarbonitrile. Another embodiment of the chemical that exhibited cell migration inhibition is 1-(4-chloro-benzoyl)-2-(4-methoxy-phenyl)-1,2-dihydro-3aH-pyrrolo[1,2-a]quinoline-3,3-dicarbonitrile.

Yet another embodiment of a method for inhibiting cell migration may include treating cells with a cell migration inhibitor having a general formula of:

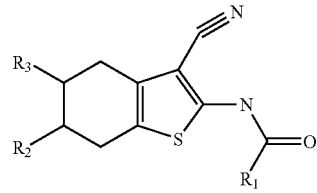

which may be an organic molecule having a molecular weight of less than about 700. $R_1$ may be selected from the group consisting of methyl, ethyl, propyl, butyl, tert-butyl, isobutyl, phenyl, benzyl, biphenyl-4-yl, 2-methyl-phenyl, 4-methyl-phenyl, 4-tert-butyl-phenyl, 2-bromo-phenyl, 3-bromo-phenyl, 4-bromo-phenyl, 2-chloro-phenyl, 3-chloro-phenyl, 4-chloro-phenyl, 2,4-dichloro-phenyl, 2,5-dichloro-phenyl, 2-fluoro-phenyl, 3-fluro-phenyl, 2,6-difluoro-phenyl, 3,4-difluoro-phenyl, 3-trifluoromethyl-phenyl, 3-iodo-phenyl, 4-acetyl-phenyl, 2-formyl-phenyl, 2-carboxy-phenyl, 3-carboxy-phenyl, 2-methoxy-phenyl, 3-methoxy-phenyl, 4-methoxy-phenyl, 3,4-dimethoxy-phenyl, 3,5-dimethoxy-phenyl, 3,4,5-trimethoxy-phenyl, 4-ethoxy-phenyl, 3,4,5-triethoxy-phenyl, 4-butoxy-phenyl, 4-phenoxymethyl, 4-phenoxy-phenyl, 4-chloro-phenoxymethyl, 2-nitro-phenyl, 3-nitro-phenyl, 4-nitro-phenyl, 3,5-dinitro-phenyl, 2-methyl-3-nitro-phenyl, 2-chloro-4-nitro-phenyl, 4-chloro-3-nitro-phenyl, 2-carboxy-5-nitro-phenyl, 4-benzoyl-phenyl, 4-cyano-phenyl, naphthalen-1-yl, 3-methoxy-napthalen-2-yl, tetrahydro-furan-2-yl, 5-bromo-furan-2-yl, 2-chloro-pyridin-3-yl, 3-carboxy-pyrazin-2-yl, 2-phenyl-quinolin-4-yl, thiophen-2-yl, phenyl-phenylsulfanyl-methyl, benzo[1,3]dioxol-5-yl, 3-(2,4-dichloro-phenoxy)-propyl, 8-allyl-2-oxo-2H-chromen-3-yl, 4-methyl-piperazin-1-ylmethyl, 5-methyl-3-trifluoromethyl-pyrazol-1-ylmethyl, 4-bromo-5-methyl-3-trifluoromethyl-pyrazol-1-ylmethyl, 4-chloro-5-methyl-3-trifluoromethyl-4H-pyrazol-1-yl-methyl, 5-methyl-3-nitro-pyrazol-1-ylmethyl, 3,5-dimethyl-4-nitro-pyrazol-1-ylmethyl, 4-bromo-5-methyl-3-nitro-pyrazol-1-ylmethyl, 3-nitro-[1,2,4]triazol-1-ylmethyl, 4-nitro-imidazol-1-ylmethyl, 5,7-diphenyl-pyrazolo[1,5-a]pyrimidin-3-yl, 6-bromo-pyrazolo[1,5-a]pyrimidin-2-yl, 3,6-dibromo-pyrazolo[1,5-a]pyrimidin-2-yl, 5-(4-ethoxy-phenyl)-7-methyl-pyrazolo[1,5-a]pyrimidin-2-yl, 5-phenyl-7-trifluoromethyl-pyrazolo[1,5-a]pyrimidin-2-yl, 3-bromo-5-phenyl-7-trifluoromethyl-pyrazolo[1,5-a]pyrimidin-2-yl, 5-(4-bromo-phenyl)-7-trifluoromethyl-pyrazolo[1,5-a]pyramidin-2-yl, 5-(4-fluoro-phenyl)-7-trifluoromethyl-pyrazolo[1,5-a]pyramidin-2-yl, 3-bromo-5-thiophen-2-yl-7-trifluoromethyl-pyrazolo[1,5-a]pyrimidin-2-yl, 3-chloro-5-phenyl-7-trifluoromethyl-pyrazolo[1,5-a]pyrimidin-2-yl, 5-furan-2- yl-7-trifluoromethyl-pyrazolo[1,5-a]pyrimidin-2-yl, 5-thiophen-2-yl-7-trifluoromethyl-pyrazolo[1,5-a]pyrimidin-2-yl, 3-chloro-6-fluoro-benzo[b]thiophen-2-yl, 4-(piperidine-1-sulfonyl)-phenyl, 4-methyl-3-(piperidine-1-sulfonyl)-phenyl, 2-chloro-5-(piperidine-1-sulfonyl)-phenyl, 5-diethylsulfamoyl-phenyl, 4-dipropylsulfamoyl-phenyl, 4-phenyl-1H-tetrazol-5-ylsulfanylmethyl, benzo[4,5]thiazolo[2,3-c][1,2,4]triazol-3-ylsulfanylmethyl, 3-(morpholine-4-sulfonyl)-phenyl, 4-(morpholine-4-sulfonyl)-phenyl, 4-bromo-5-(morpholine-4-sulfonyl)-phenyl, 4-chloro-5-(morpholine-4-sulfonyl)-phenyl, and 2,4-dichloro-5-(morpholine-4-sulfonyl)-phenyl.

$R_2$ may be selected from the group consisting of hydrogen, methyl, tert-butyl, and 1,1-dimethyl-propyl. $R_3$ may be selected from the group consisting of hydrogen and methyl. One embodiment of the chemical that exhibited cell migration inhibition is N-(3-cyano-4,5,6,7-tetrahydro-benzo[b]thiophen-2-yl)-3-iodo-benzamide.

In an additional embodiment, a method for inhibiting cell migration may include treating cells with a cell migration inhibitor having a general formula of:

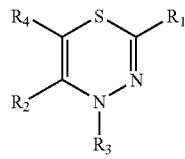

which may be an organic molecule having a molecular weight of less than about 700. $R_1$ may be selected from the group consisting of 4-bromo-benzoylamino, (adamantan-2-yl-hydroxy-methyl)-amino, and phenylamino. $R_2$ may be selected from the group consisting of dihydro-benzo[1,4]dioxin-6-yl, p-chloro-phenyl, p-methyl-phenyl, phenyl, and p-methoxy-phenyl. $R_3$ may be selected from the group consisting of hydrogen, 2-propenyl, and phenyl. $R_4$ may be selected from the group consisting of hydrogen and methyl. In one embodiment, the chemical is [5-(2,3-dihydro-benzo[1,4]dioxin-6-yl)-4H-[1,3,4]thiadiazin-2-yl]-phenyl-amine.

Another embodiment relates to a pharmaceutical composition that includes any one of the cell migration inhibitors described herein. The pharmaceutical composition also includes a chemotherapeutic agent. The chemotherapeutic agent may include, but is not limited to, an alkylating agent, an antitumor antibiotic, an antimetabolite, an antimicrotubule agent, a spindle-tubule inhibitor, a topoisomerase inhibitor, a hormonal agent, a biological agent, and a granulocyte-colony stimulating factor. In an embodiment, the pharmaceutical composition may include more than one of the cell migration inhibitors described herein and/or more than one of the above chemotherapeutic agents. The pharmaceutical composition may also include a pharmaceutically acceptable carrier.

In one embodiment, the inhibitor is 4'-propyl-bicyclohexyl-4-carboxylic acid, and the chemotherapeutic agent is 1,3-bis(2-chloroethyl)-1-nitrosourea. In another embodiment, the inhibitor is 4-methyl-3-nitro-benzoic acid, and the chemotherapeutic agent is 1,3-bis(2-chloroethyl)-1-nitrosourea. In an alternative embodiment, the inhibitor is 4-methyl-3-nitro-benzoic acid, and the chemotherapeutic agent is paclitaxel. Another embodiment of a pharmaceutical composition includes the cell migration inhibitor 1-(4-chloro-benzoyl)-2-(3,4-dimethoxy-phenyl)-1,2-dihydro-3aH-pyrrolo[1,2-a]quinoline-3,3-dicarbonitrile and the chemotherapeutic agent gemcytabine. An additional embodiment of a pharmaceutical composition includes the cell migration inhibitor 1-(4-chloro-benzoyl)-2-(4-methoxy-phenyl)-1,2-dihydro-3-aH-pyrrolo[1,2-a]quinoline-3,3-dicarbonitrile and gemcytabine.

An additional embodiment relates to a method for treating an individual having cancer. The method may include administering a cell migration inhibitor and a chemotherapeutic agent to the individual to inhibit migration of cancer cell. Inhibiting cell migration may increase cell division. In this manner, the cell migration inhibitor and the chemotherapeutic agent in combination may have increased efficacy compared to the chemotherapeutic agent alone due to the increased cell division. The cell migration inhibitor may include any of the inhibitors described herein. For example, the cell migration inhibitor may be an organic molecule having a molecular weight of less than about 700.

Further embodiments relate to a method for treating an individual having cancer. The method may include administering a cell migration inhibitor and a chemotherapeutic agent to the individual. The cell migration inhibitor may be any one of the cell migration inhibitors described herein. The chemotherapeutic agent may be any one of the chemotherapeutic agents described herein. In addition, the method may include administering more than one cell migration inhibitor and/or more than one chemotherapeutic agent to the individual. The cell migration inhibitor and the chemotherapeutic agent may be administered using any method known in the art (i.e., orally, intravenously, etc.).

Another embodiment relates to a method for identifying a treatment for an individual having cancer. The method may include establishing a tissue culture of the cancer of the individual. The method may also include identifying a cell migration inhibitor for the cancer based on the tissue culture. In addition, the method may include identifying a chemotherapeutic agent that has efficacy in combination with the cell migration inhibitor. In an additional embodiment, the method may include administering the cell migration inhibitor and the chemotherapeutic agent to the individual.

A method for treating a disease, which may be at least partially attributable to abnormal cell migration, is also provided. The disease may be, but is not limited to, autoimmune disease or cardiovascular disease. The method may include altering abnormal cell migration of the disease by administering a cell migration inhibitor to an individual having the disease. The cell migration inhibitor may include any of the cell migration inhibitors described herein. The method may also include treating the disease by administering a pharmaceutical agent to the individual. The pharmaceutical agent may include any pharmaceutical agent appropriate for treatment of a disease as described above.

The compounds described herein are arylating agents. Therefore, other relatively small organic molecules that are arylating agents may also exhibit cell migration. An embodiment of a method for inhibiting cell migration may include treating cells with a cell migration inhibitor that is an arylating agent. Another embodiment relates to a pharmaceutical composition that includes one or more cell migration inhibitors, of which at least one is an arylating agent, and one or more chemotherapeutic agents. The chemotherapeutic agents may include any chemotherapeutic agents known in the art. The pharmaceutical composition may also include a pharmaceutically acceptable carrier. An additional embodiment relates to a method for treating an individual having cancer that includes administering a cell migration inhibitor that is an arylating agent and a chemotherapeutic agent to the individual. The method may be carried out as described herein.

In alternative embodiments, other compounds such as monoclonal antibodies and natural products may also exhibit cell migration. An embodiment of a method for inhibiting cell migration may include treating cells with a cell migration inhibitor that is a monoclonal antibody or a natural product. Another embodiment relates to a pharmaceutical composition that includes one or more cell migration inhibitors, of which at least one is a monoclonal antibody or a natural product, and one or more chemotherapeutic agents. The chemotherapeutic agents may include any chemotherapeutic agents known in the art. The pharmaceutical composition may also include a pharmaceutically acceptable carrier. An additional embodiment relates to a method for treating an individual having cancer that includes administering a cell migration inhibitor that is a monoclonal antibody or a natural product and a chemotherapeutic agent to the individual. The method may be carried out as described herein.

BRIEF DESCRIPTION OF THE DRAWINGS

Other objects and advantages of the invention will become apparent upon reading the following detailed description and upon reference to the accompanying drawings in which:

FIG. 1 depicts a perspective bottom view of a guided cell sedimentation apparatus;

Figure 1A:
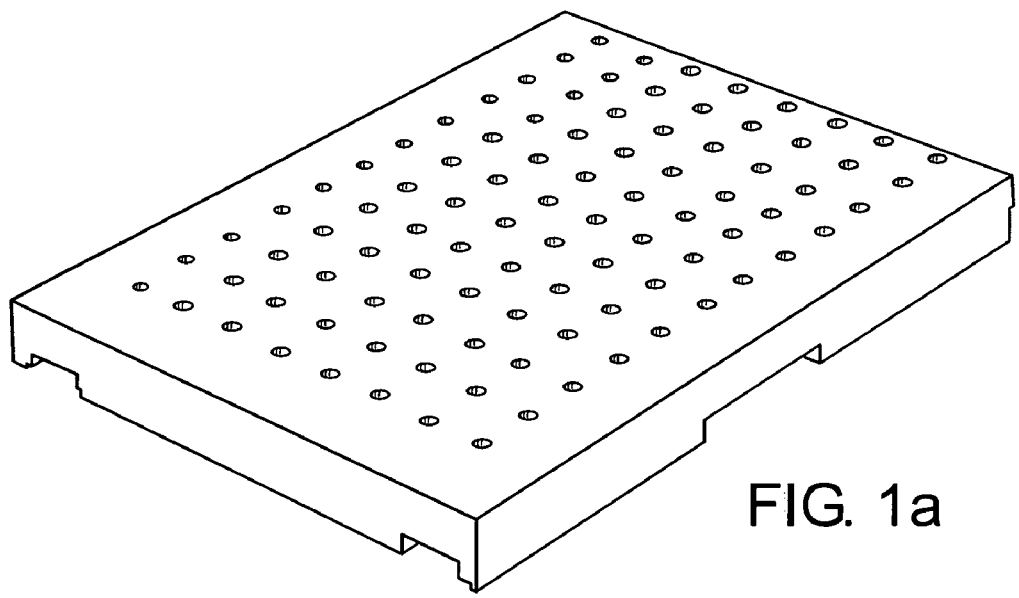
FIG. 1a depicts a perspective top view of a portion of a 96 channel manifold.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1B:
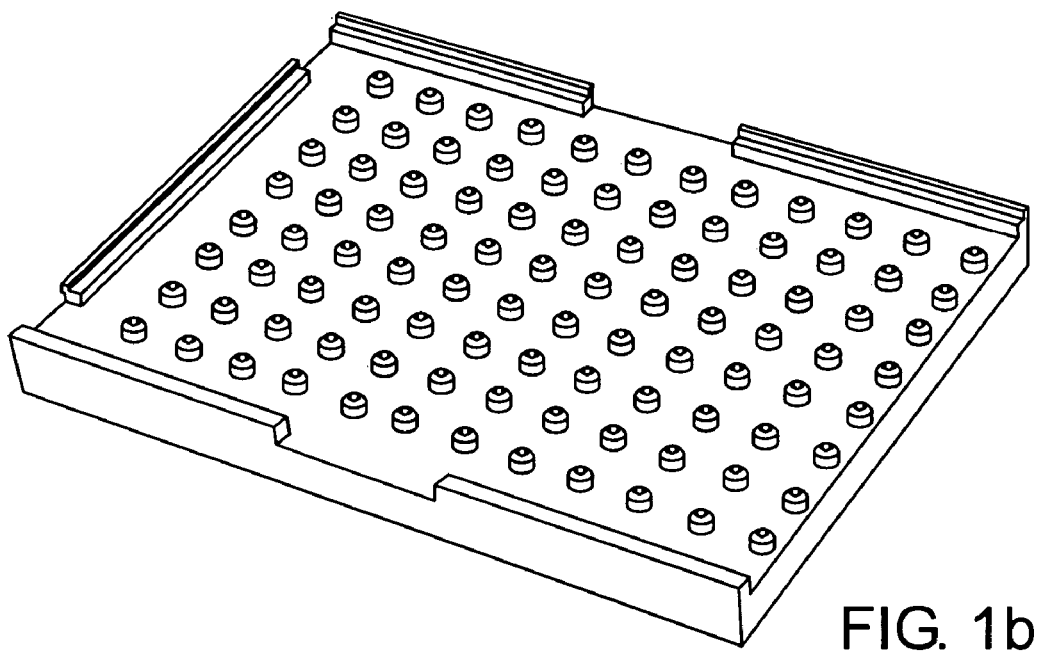
FIG. 1b depicts a perspective bottom view of a portion of the 96 channel manifold.

Turning now to the drawings, FIG. 1 illustrates a perspective bottom view of a guided cell sedimentation apparatus. The apparatus includes manifold 10. Manifold 10 has lateral dimensions that are larger than a substrate onto which cells are to be deposited. Manifold 10 may be formed of a solid block of material such as stainless steel. The material may provide a heat sink such that a relatively low temperature may be maintained by the manifold. The manifold includes channels 12. The channels are formed for a commercially available Teflon-masked slide. The channels are disposed at predetermined intervals across the manifold. Although 10 channels are illustrated in FIG. 1, it is to be understood that the manifold may include any number of such channels. For example, the manifold may include 96 channels arranged in a 8×12 two-dimensional array of channels. FIG. 1a illustrates a perspective top view of a portion of a 96 channel manifold, and FIG. 1b illustrates a perspective bottom view of a portion of the 96 channel manifold. The manifold illustrated in FIGS. 1a and 1b may be configured as described herein. The channels may have a diameter of about 1.0 mm and may have a length approximately equal to a height of the manifold. An overall height of the manifold is less than 2.5 cm, which is the theoretical limiting distance that surface tension will bring physiological fluid up the channel. The height of the manifold is preferably 1.25 cm.

Figure 2:
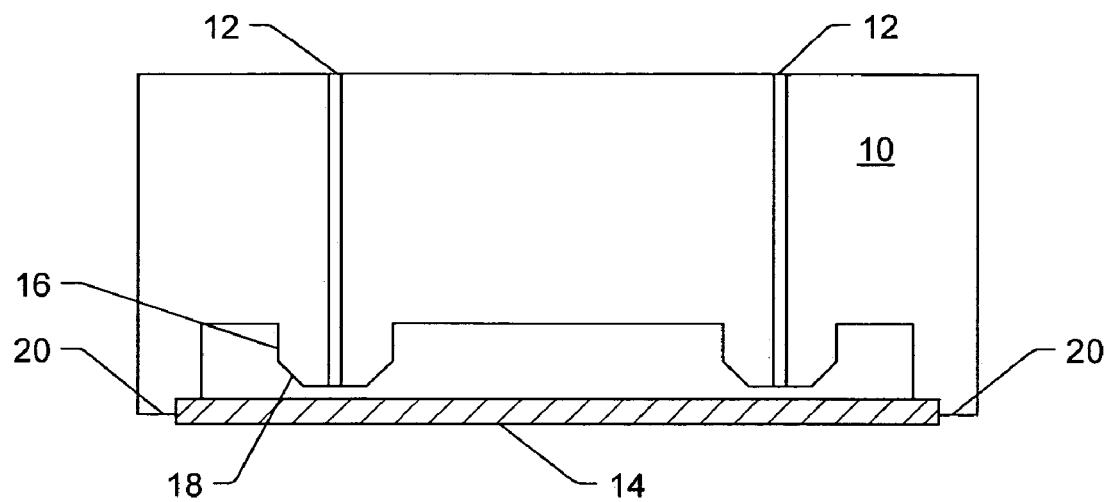
FIG. 2 depicts a cross-section view of the guided cell sedimentation apparatus coupled to a substrate.

FIG. 2 illustrates a cross-sectional view of the guided cell sedimentation apparatus of FIG. 1 coupled to substrate 14. The substrate is a microscope slide. As shown in FIG. 2, channels 12 extend from a top surface of manifold 10 to slightly above an upper surface of substrate 14 when the manifold is coupled to the substrate. Bottom portion 16 of channels 12 extends beyond a lower surface of the manifold such that each channel is isolated from the other channels. Bottom portion 16 includes bevel 18 proximate lower outer lateral edges of the channel. Bevel 18 reduces capillary forces proximate the exit of the channel.

Manifold 10 is coupled to substrate 14 by overhanging tabs 20 formed across two bottom edges of the manifold. The overhanging tabs are formed by milling the manifold. As shown in FIG. 1, the manifold also includes overhanging tab 22 formed on a third bottom edge of the manifold. The overhanging tabs are used to position the manifold on the slide and to prevent shifting of the manifold on the substrate in two lateral directions. The apparatus may be further configured as described in U.S. Pat. No. 5,998,160 to Berens, which is incorporated by reference as if fully set forth herein. An example of an appropriate cell sedimentation manifold is available from Creative Scientific Methods, Inc., Phoenix, Ariz.

Figure 3:
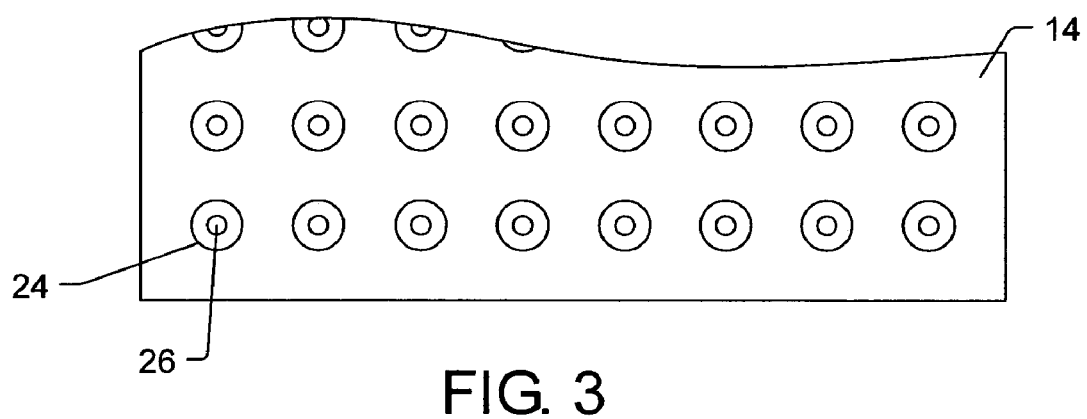
FIG. 3 depicts a partial top view of a substrate onto which cells are deposited.

The guided cell sedimentation apparatus may be used to deposit cells onto a substrate at predetermined locations. A manifold and a substrate as described above may be stored in autoclave bags and steam autoclaved for about 1 hour to sterilize the manifold. The manifold may then be stored at about 4° C. until testing is to be performed. FIG. 3 illustrates a top schematic view of substrate 14. Prior to deposition, the surface of substrate 14 onto which the cells will be deposited is treated according to the experiment to be performed. For example, about 20 μl of a surface coating may be added to each well and incubated for about 1 hour at about 37° C. Just prior to deposition of the cells, Teflon-defined wells 24 on the substrate are hydrated in a culture media appropriate for the cells under study. Approximately 50 μl of culture media is deposited onto each well. Manifold 10, pre-cooled to 4° C. is coupled to the substrate, as shown in FIG. 2, such that overhanging tabs 20 and 22 secure the manifold to the substrate. A small aliquot of the culture media (i.e., about 1 μl) is aspirated from each channel of the manifold to eliminate air bubbles within the channels.

The cells are harvested from a culture according to any method known in the art. The cell concentration is adjusted to about 2000 cells/μl. An appropriate cell concentration may vary depending on the cell type. The cells are deposited into each channel in a volume of about 1 μl. The number of cells deposited onto the substrate varies depending upon the physical characteristics of the cells under study. For example, about 500 to about 3000 cells are deposited in each location. The manifold, substrate, and cells should stand undisturbed for a period of time of, for example, about 30 minutes. During the time, the cells will sediment. Sedimentation is generally defined as a process in which gravity causes heavier objects in a suspension to settle to the lowest part of the system. As used herein, sedimentation refers to the process in which gravity causes cells to settle through a standing column of culture media that fills the channels in the manifold. Forces greater than gravity should be avoided to prevent damage of the cells.

The manifold, substrate, and cells are transferred to a controlled temperature and atmosphere tissue culture incubator for several hours to overnight to allow the cells to attach to the surface of the substrate. Appropriate conditions for the incubator are about 37° C., about 37% carbon dioxide ($CO_2$), and humidified air. The cells sediment onto a defined location at the bottom of the channel. Therefore, when the manifold is removed from the substrate, the cells are deposited as discs 26 of cells at predetermined locations on the substrate, as shown in FIG. 3. Such sedimentation of cells may further include any other steps of the methods as described by Berens. After the cells are attached and the manifold has been removed, the cells in each well may be re-fed with an appropriate solution.

The guided cell sedimentation apparatus provides a number of advantages for the study of cell migration. For example, living cells may be deposited onto a predetermined area of a substrate while preserving the viability and function of the cells remaining intact. Many different kinds of cells may also be easily deposited onto a substrate thereby making the study of cell migration very easy. In addition, the apparatus may be used to determine the effects of chemicals on cell migration in relatively small quantities. Additionally, the effects of the chemicals on cell migration may be examined as the cells migrate using, for example, an inverted microscope. Furthermore, depositing cells in predetermined, defined, locations provides the ability to use video microscopic analysis of the serial motion of the cells. Therefore, the guided cell sedimentation apparatus described above enables intensive studies of cell migration at both the cellular and gene expression levels of analysis thereby providing a new and unexplored opportunity in this area of medical research. Furthermore, the results obtained using the guided cell sedimentation apparatus are comparable to other methods such as the Boyden Chamber and the Scratch Wound Assay, which are discussed in more detail above.

The methods and systems described herein can be used to examine cell migration inhibition of various types of cancer cells. The various types of cancers include, but are not limited to, glioma (brain cancer), breast cancer, breast cancer with metastasis to the brain, lung/bronchus cancer, lung cancer with metastasis to the brain, melanoma (skin cancer), melanoma with metastasis to the brain, other central nervous system cancer, pancreatic cancer, stomach cancer, liver cancer, colon/rectum cancer, cervix uteri cancer, corpus uteri cancer, ovarian cancer, prostate cancer, bladder cancer, mouth/pharynx cancer, esophagus cancer, leukemia, and Non-Hodgkin's lymphoma.

Cell migration may be monitored over time by monitoring the location of individual cells over time or measuring the radius of a circle surrounding the cells over time. Measuring the radius of a circle surrounding the cells may include detecting peripheral cells, which will migrate in an overall net perpendicular direction relative to the outer edge of the circle, to determine an outer edge of the migrating cells. The peripheral cells are easily detected because the cells can be deposited as a confluent monolayer within a predetermined area. To measure the radius as a function of time, low magnification optics may be used to image the entire area occupied by the cells. For such a measurement, an initial area of the cells must be smaller than a field of view of the low magnification optics because the area occupied by the cells will increase over time. Alternatively, designations such as numbers can be assigned to individual cells such that cells may be counted or characterized within the deposited sample of cells. For example, a high-powered objective lens may be used to identify, count, or characterize individual cells. Monitoring individual cells does not limit the initial area of the cells.

In an embodiment, a kit for measuring inhibition of cell migration is also provided. The kit may include a guided cell sedimentation apparatus, cancer cells, and one or more chemicals from a library. The apparatus may be configured such that the cancer cells can be deposited at predetermined locations on a substrate. The apparatus may be further configured as described herein. The cancer cells may include any of the cancer cells described herein or any cancer cells known in the art. The one or more chemicals may include organic molecules having a molecular weight of less than about 700, monoclonal antibodies, and/or natural products. The cancer cells can be treated with the one or more chemicals on the substrate, and a cell migration rate of the cancer cells can be measured on the substrate. The kit may also be used for assessing synergistic killing of cancer cells by a combination of the one or more chemicals and a chemotherapeutic agent. One or more chemotherapeutic agents may be included in the kit, and the chemotherapeutic agents may include any chemotherapeutic agent described herein or known in the art.

Figure 4:
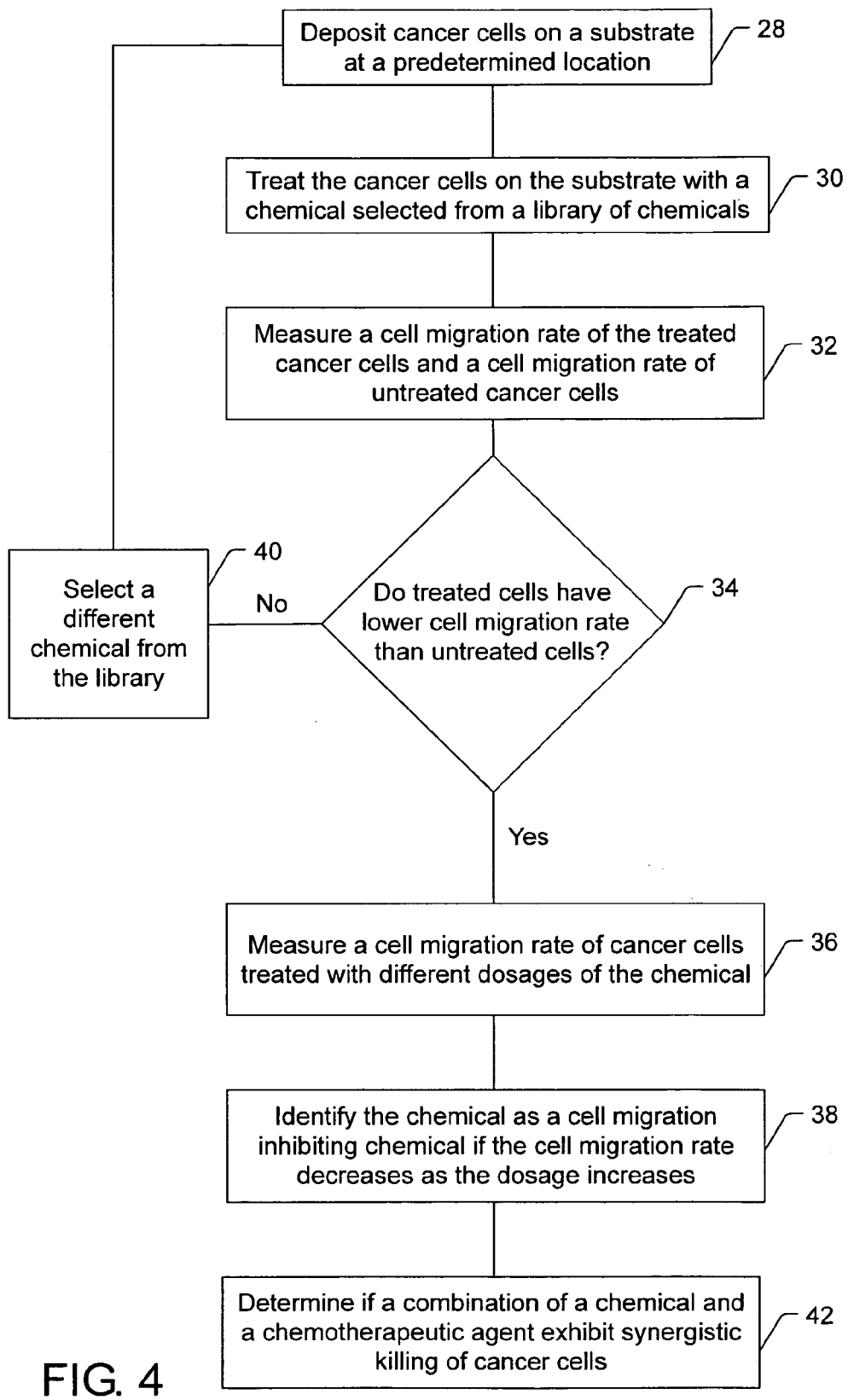
FIG. 4 is a flow chart illustrating an embodiment of a method for identifying a chemical that inhibits cell migration.

FIG. 4 illustrates a flow chart of an embodiment of a method for identifying a chemical that inhibits cell migration. The method may include depositing cancer cells on a substrate at a predetermined location, as shown in step 28. An appropriate amount of cells for a cell migration experiment may be about 2000 cells to about 3000 cells in about 25 µl of media. The cancer cells may include glioma cancer cells, melanoma cancer cells, breast cancer cells, pancreatic cancer cells, lung cancer cells, or cells of any other type of cancer as described herein. In addition, the cells may include Human Umbilical Veil Endothelial Cells (HUVEC). These cells are a model system for detecting potential angiogenesis inhibitors and for detecting inhibitors of vascular endothelial restenosis. These cells are available from, for example, Cell Applications, Inc., San Diego, Calif. Depositing the cancer cells may be performed using guided cell sedimentation and an apparatus described above.

The method may also include treating the cancer cells on the substrate subsequent to sedimentation with a chemical selected from a library of chemicals, as shown in step 30. The amount of the chemical used to treat the cancer cells may vary from picograms of the chemical to nanograms of the chemical. The library of chemicals may be randomly selected from a list of chemicals that are novel or commercially available. The chemicals in the library may include organic molecules having a molecular weight of less than about 700. The library of chemicals may also be limited to organic molecules having a molecular weight of less than about 500. In an embodiment, all of the chemicals in the library may include organic molecules. It is to be understood, however, that the methods described herein may be used to measuring the cell migration rate of cancer cells treated with any molecule known in the art having any molecular weight. For example, the library of chemicals may include monoclonal antibodies and/or natural products. As used herein, "natural products" is used to refer to any chemical that can be found in nature or that may be formed using a semi-synthetic process from a chemical found in nature. The chemicals in the library are molecules that are non-toxic to both treatment and control cells.

As shown in step 32, the method may include measuring a cell migration rate of cancer cells treated with a chemical selected from a library of chemicals and a cell migration rate of untreated cancer cells. Measuring the cell migration rate may be performed by measuring a distance that the cancer cells migrate radially from an approximate center of a sample of the cancer cells. For example, measuring the cancer cells may include measuring the radius of a circle surrounding the cells over time as described above. The migration rate may be measured as described above and may be expressed in units of µm/day. The method may also include measuring an additional property of the cancer cells treated with the chemical and the cancer cells in the untreated control sample. The additional property may include, for example, chemotaxis, haptotaxis, galvanotaxis, chemotropism, and/or chemokinesis.

As shown in step 34, the method may include determining if the treated cancer cells have a lower cell migration rate than the untreated cancer cells. If the treated cancer cell have a lower cell migration rate than the untreated cancer cells, then the method may include measuring a cell migration rate of cancer cells treated with different dosages of the chemical, as shown in step 36. A dose response curve may be generated using target cell line samples treated with different dosages. In addition, the method may include identifying the chemical as a cell migration inhibiting chemical if the cell migration rate decreases as the dosage increases, as shown in step 38. If the treated cancer cells do not have a lower cell migration rate than the untreated cancer cell, the method may include selecting a different chemical from the library as shown in step 40 and repeating at least steps 28-34 for the different chemical.

Such a method may also be easily performed on a plurality of chemicals selected from a library of chemicals because the guided cell sedimentation apparatus described above provides high throughput screening of cell migration at a relatively low cost. For example, cells may be deposited onto a plurality of predetermined locations on a substrate as described above. In addition, different samples of the cancer cells may be treated with different chemicals selected from the library, and a cell migration rate of each sample may be measured. The cell migration rate of an untreated control sample of the cancer cells may also be measured. The cell migration rates may be used to compare the relative ability of the chemicals to inhibit cell migration. One or more of the different chemicals having cell migration rates lower than at least the cancer cells of the untreated control sample may be selected. The cell migration rates of cancer cells treated with different chemicals may also be compared. For example, an average cell migration rate of all samples of the cancer cells may be determined and samples having a cell migration rate lower than the average by a predetermined value may be selected. Any other comparison may also be used to select chemicals as potential cell migration inhibitors. The method may also include measuring a cell migration rate of cancer cells treated with different dosages of the selected chemicals. In addition, the method may include identifying one or more of the selected chemicals as cell migration inhibiting chemicals if the cell migration rate of the cancer cells decreases as the dosage increases.

All of the methods described herein may be used to study the effects of chemicals on the migration of cancer cells or other migratory cells. For example, a method for identifying a chemical that alters cell migration may include measuring the cell migration of cells treated with the chemical and the cell migration rate of untreated cells. The method may also include measuring the cell migration rate of cells treated with different dosages of the chemical if the treated cell have a different cell migration rate than the untreated cell. In addition, the method may include identifying the chemical as a cell migrating altering chemical if the cell migration rate varies depending upon the dosage. In this manner, the methods described herein may also be used for wound healing. Chemicals that alter cell migration may also be used to identify chemicals that increase cell migration. Chemicals that increase cell migration may be used to treat a disease, of which at least part of the disease is attributed to abnormal cell migration. Examples of such diseases include, but are not limited to, autoimmune disease and cardiovascular disease.

An embodiment of a chemical that has been identified as a cell migration inhibitor has a general formula of:

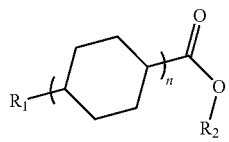

The chemical is an organic molecule having a molecular weight of less than about 700. In the above general formula, n is 1 or 2. $R_1$ is selected from the group consisting of methyl, propyl, butyl, pentyl, hexyl, tert-butyl, acetoxy, phenyl, biphenyl-4-yl, 4-iodo-phenyl, and 4-pentyl-phenoxycarboynylmethyl. $R_2$ is selected from the group consisting of hydrogen, 4-acetyl-amino, 4-(2-cyano-ethyl)-phenyl, 4-propenyl-phenyl, 4-pentyl-phenyl, 4-bromo-phenyl, 4-chloro-phenyl, 3-chloro-4-fluoro-phenyl, 4-acetyl-phenyl, 4-hydroxy-phenyl, 4-ethoxy-phenyl, 4-oxtyloxy-phenyl, 2,3-dicyano-4-hexyloxy-phenyl, 4-butoxy-2,3-dichloro-phenyl, 4-pentanoyl-phenyl, 4-cyano-phenyl, biphenyl-4-yl, 4'-methyl-biphenyl-4-yl, 4'-cyano-biphenyl-4-yl, 2-(4-bromo-phenyl)-2-oxo-ethyl, 2-(4'-bromo-biphenyl-4-yl)-2-oxo-ethyl, 4-cyclohexanecarbonyloxy-phenyl, and 4-benzoic acid ethyl ester. One embodiment of the chemical that exhibited cell migration inhibition is 4'-propyl-bicyclohexyl-4-carboxylic acid. Chemicals having the above general formula may inhibit cell migration of various types of cancer cells such as glioma cancer cells.

Additional examples of chemicals having the above general formula that may inhibit cell migration include, but are not limited to:
1) 4-propyl-cyclohexanecarboxylic acid,
2) 4-acetoxy-cyclohexanecarboxylic acid,
3) 4-pentyl-cyclohexanecarboxylic acid,
4) 4-phenyl-cyclohexanecarboxylic acid,
5) cyclohexanecarboxylic acid 4-acetyl-phenyl ester,
6) 4-methyl-cyclohexanecarboxylic acid 4-chloro-phenyl ester,
7) 4'-butyl-bicyclohexyl-4-carboxylic acid,
8) 4-biphenyl-4-yl-cyclohexanecarboxylic acid,
9) 4'-pentyl-bicyclohexyl-4-carboxylic acid,
10) 4-butyl-cyclohexanecarboxylic acid 4-cyano-phenyl ester,
11) 4-pentyl-cyclohexanecarboxylic acid 4-hydroxy-phenyl ester,
12) 4-methyl-cyclohexanecarboxylic acid 4-pentanoyl-phenyl ester,
13) 4-methyl-cyclohexanecarboxylic acid 4'-methyl-biphenyl-4-yl ester,
14) 4-butyl-cyclohexanecarboxylic acid 4-acetylamino-phenyl ester,
15) 4-hexyl-cyclohexanecarboxylic acid 4-propenyl-phenyl ester,
16) 4-(4-iodo-phenyl)-cyclohexanecarboxylic acid,
17) 4-hexyl-cyclohexanecarboxylic acid 4-ethoxy-phenyl ester,
18) 4-butyl-cyclohexanecarboxylic acid biphenyl-4-yl ester,
19) 4-tert-butyl-cyclohexanecarboxylic acid 4-bromo-phenyl ester,
20) 4-hexyl-cyclohexanecarboxylic acid 4-(2-cyano-ethyl)-phenyl ester,
21) 4-tert-butyl-cyclohexanecarboxylic acid 4'-methyl-biphenyl-4-yl ester,
22) 4-(4-hexyl-cyclohexanecarbonyloxy)-benzoic acid ethyl ester,
23) 4-butyl-cyclohexanecarboxylic acid 4'-cyano-biphenyl-4-yl ester,
24) 4-pentyl-cyclohexanecarboxylic acid 4'-cyano-biphenyl-4-yl ester,
25) 4'-propyl-bicyclohexyl-4-carboxylic acid 3-chloro-4-fluoro-phenyl ester,
26) 4-butyl-cyclohexanecarboxylic acid 2-(4-bromo-phennyl)-2-oxo-ethyl ester,
27) 4'-pentyl-bicyclohexyl-4-carboxylic acid 3-chloro-4-fluoro-phenyl ester,
28) 4-hexyl-cyclohexanecarboxylic acid 4-octyloxy-phenyl ester,
29) 4'-propyl-bicyclohexyl-4-carboxylic acid 2-(4-bromo-phenyl)-2-oxo-ethyl ester,
30) 4-hexyl-cyclohexanecarboxylic acid 2,3-dicyano-4-heptyloxy-phenyl ester,
31) 4-butyl-cyclohexanecarboxylic acid 2-(4'-bromo-biphenyl-4-yl)-2-oxo-ethyl ester,
32) cyclohexane-1,3-dicarboxylic acid bis-(4-pentyl-phenyl) ester,
33) 4'-propyl-bicyclohexyl-4-carboxylic acid 2,3-dicyano-4-hexyloxy-phenyl ester, and
34) 4'-pentyl-bicyclohexyl-4-carboxylic acid 4-butoxy-2,3-dichloro-phenyl ester.

An additional embodiment of a chemical that has been identified as a cell migration inhibitor has a general formula of:

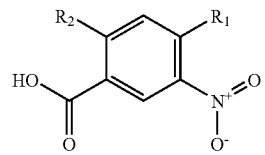

This chemical is also organic molecule having a molecular weight of less than about 700. $R_1$ is selected from the group consisting of hydrogen, methyl, methoxy, bromo, amino, 2-hydroxy-ethylamino, and 3-hydroxy-propylamino. $R_2$ is selected from the group consisting of hydrogen and acetylamino. In one embodiment, $R_1$ or $R_2$ is hydrogen. In another embodiment, $R_1$ and $R_2$ are acyclic groups. In an additional embodiment, $R_1$ and $R_2$ are not nitro groups. One embodiment of the chemical that exhibited cell migration inhibition is 4-methyl-3-nitro-benzoic acid. Chemicals having the above general formula may inhibit cell migration of various types of cancer cells such as breast cancer cells, melanoma cancer cells, and lung cancer cells.

Additional examples of chemicals having the above general formula that may exhibit cell migration inhibition include, but are not limited to:
1) 4-(2-hydroxy-ethylamino)-3-nitro-benzoic acid,
2) 4-chloro-3-nitro-benzoic acid,
3) 2-acetylamino-5-nitro-benzoic acid,
4) 3-nitro-benzoic acid,
5) 4-(3-hydroxy-propylamino)-3-nitro-benzoic acid,
6) 2-amino-5-nitro-benzoic acid,
7) 4-amino-3-nitro-benzoic acid,
8) 4-methoxy-3-nitro-benzoic acid, and
9) 4-bromo-3-nitro-benzoic acid.

Another embodiment of a chemical that has been identified as a cell migration inhibitor has a general formula of:

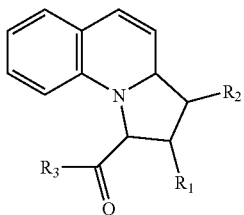

which is an organic molecule having a molecular weight of less than about 700. $R_1$ is selected from the group consisting of phenyl, 3,4-dimethoxy-phenyl, benzo[1,3]dioxol-5-yl, 4-fluoro-phenyl, and 4-methoxy-phenyl. $R_2$ is selected from the group consisting of 4-(2,2-dicyano-1-cyclopropyl-vinyl) and dicyano. $R_3$ is selected from the group consisting of 4-chlorophenyl, phenyl, and cyclopropyl. One embodiment of the chemical that exhibited cell migration inhibition is 1-(4-chloro-benzoyl)-2-(3,4-dimethoxy-phenyl)-1,2-dihydro-3aH-pyrrolo[1,2-a]quinoline-3,3-dicarbonitrile. Another embodiment of the chemical that exhibited cell migration inhibition is 1-(4-chloro-benzoyl)-2-(4-methoxy-phenyl)-1,2-dihydro-3aH-pyrrolo[1,2-a]quinoline-3,3-dicarbonitrile. Chemicals having the above general formula may inhibit cell migration of various types of cancer cells such as pancreatic cancer cells.

Additional examples of chemicals having the above general formula that may exhibit cell migration inhibition include, but are not limited to:
1) 2-{[1-(4-chloro-benzoyl)-2-phenyl-1,2,3,3a-tetrahydropyrrolo[1,2-a]quinoline-3-yl]-cyclopropyl-methylene}-malononitrile,
2) 1-bezoyl-2-(3,4-dimethoxy-phenyl)-1,2-dihydro-3aH-pyrrolo[1,2-a]quinoline-3,3-dicarbonitrile,
3) 2-benzo[1,3]dioxol-5-yl-1-cycloprpanecarbonyl-1,2-dihydro-3aH-pyrrolo[1,2-a]quinoline-3,3-dicarbonitrile, and
4) 1-(4-chloro-benzoyl)-2-(4-fluoro-phenyl)-1,2-dihydro-3aH-pyrrolo[1,2-a]quinoline-3,3-dicarbonitrile.

Yet another embodiment of a chemical that has been identified as a cell migration inhibitor has a general formula of:

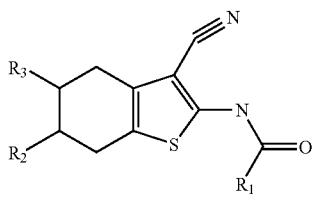

which is an organic molecule having a molecular weight of less than about 700. $R_1$ is selected from the group consisting of methyl, ethyl, propyl, butyl, tert-butyl, isobutyl, phenyl, benzyl, biphenyl-4-yl, 2-methyl-phenyl, 4-methyl-phenyl, 4-tert-butyl-phenyl, 2-bromo-phenyl, 3-bromo-phenyl, 4-bromo-phenyl, 2-chloro-phenyl, 3-chloro-phenyl, 4-chloro-phenyl, 2,4-dichloro-phenyl, 2,5-dichloro-phenyl, 2-fluoro-phenyl, 3-fluro-phenyl, 2,6-difluoro-phenyl, 3,4-difluoro-phenyl, 3-trifluoromethyl-phenyl, 3-iodo-phenyl, 4-acetyl-phenyl, 2-formyl-phenyl, 2-carboxy-phenyl, 3-carboxy-phenyl, 2-methoxy-phenyl, 3-methoxy-phenyl, 4-methoxy-phenyl, 3,4-dimethoxy-phenyl, 3,5-dimethoxy-phenyl, 3,4,5-trimethoxy-phenyl, 4-ethoxy-phenyl, 3,4,5-tri ethoxy-phenyl, 4-butoxy-phenyl, 4-phenoxymethyl, 4-phenoxy-phenyl, 4-chloro-phenoxymethyl, 2-nitro-phenyl, 3-nitro-phenyl, 4-nitro-phenyl, 3,5-dinitro-phenyl, 2-methyl-3-nitro-phenyl, 2-chloro-4-nitro-phenyl, 4-chloro-3-nitro-phenyl, 2-carboxy-5-nitro-phenyl, 4-benzoyl-phenyl, 4-cyano-phenyl, naphthalen-1-yl, 3-methoxy-napthalen-2-yl, tetrahydro-furan-2-yl, 5-bromo-furan-2-yl, 2-chloro-pyridin-3-yl, 3-carboxy-pyrazin-2-yl, 2-phenyl-quinolin-4-yl, thiophen-2-yl, phenyl-phenylsulfanyl-methyl, benzo[1,3]dioxol-5-yl, 3-(2,4-dichloro-phenoxy)-propyl, 8-allyl-2-oxo-2H-chromen-3-yl, 4-methyl-piperazin-1-ylmethyl, 5-methyl-3-trifluoromethyl-pyrazol-1-ylmethyl, 4-bromo-5-methyl-3-trifluoromethyl-pyrazol-1-ylmethyl, 4-chloro-5-methyl-3-trifluoromethyl-4H-pyrazol-1-yl-methyl, 5-methyl-3-nitro-pyrazol-1-ylmethyl, 3,5-dimethyl-4-nitro-pyrazol-1-ylmethyl, 4-bromo-5-methyl-3-nitro-pyrazol-1-ylmethyl, 3-nitro-[1,2,4]triazol-1-ylmethyl, 4-nitro-imidazol-1-ylmethyl, 5,7-diphenyl-pyrazolo[1,5-a]pyrimidin-3-yl, 6-bromo-1H-pyrazolo[1,5-a]pyrimidin-2-yl, 3,6-dibromo-1H-pyrazolo[1,5-a]pyrimidin-2-yl, 5-(4-ethoxy-phenyl)-7-methyl-pyrazolo[1,5-a]pyrimidin-2-yl, 5-phenyl-7-trifluoromethyl-pyrazolo[1,5-a]pyrimidin-2-yl, 3-bromo-5-phenyl-7-trifluoromethyl-pyrazolo[1,5-a]pyrimidin-2-yl, 5-(4-bromo-phenyl)-7-trifluoromethyl-pyrazolo[1,5-a]pyramidin-2-yl, 5-(4-fluoro-phenyl)-7-trifluoromethyl-pyrazolo[1,5-a]pyramidin-2-yl, 3-bromo-5-thiophen-2-yl-7-trifluoromethyl-pyrazolo[1,5-a]pyrimidin-2-yl, 3-chloro-5-phenyl-7-trifluoromethyl-pyrazolo[1,5-a]pyrimidin-2-yl, 5-furan-2-yl-7-trifluoromethyl-pyrazolo[1,5-a]pyrimidin-2-yl, 5-thiophen-2-yl-7-trifluoromethyl-pyrazolo[1,5-a]pyrimidin-2-yl, 3-chloro-6-fluoro-benzo[b]thiophen-2-yl, 4-(piperidine-1-sulfonyl)-phenyl, 4-methyl-3-(piperidine-1-sulfonyl)-phenyl, 2-chloro-5-(piperidine-1-sulfonyl)-phenyl, 5-diethylsulfamoyl-phenyl, 4-dipropylsulfamoyl-phenyl, 4-phenyl-1H-tetrazol-5-ylsulfanylmethyl, benzo[4,5]thiazolo[2,3-c][1,2,4]triazol-3-ylsulfanylmethyl, 3-(morpholine-4-sulfonyl)-phenyl, 4-(morpholine-4-sulfonyl)-phenyl, 4-bromo-5-(morpholine-4-sulfonyl)-phenyl, 4-chloro-5-(morpholine-4-sulfonyl)-phenyl, and 2,4-dichloro-5-(morpholine-4-sulfonyl)-phenyl.

$R_2$ is selected from the group consisting of hydrogen, methyl, tert-butyl, and 1,1-dimethyl-propyl. $R_3$ is selected from the group consisting of hydrogen and methyl. One embodiment of the chemical that exhibited cell migration inhibition is N-(3-cyano-4,5,6,7-tetrahydro-benzo[b]thiophen-2-yl)-3-iodo-benzamide.

Additional examples of chemicals having the above general formula that may exhibit cell migration inhibition include, but are not limited to:
1) N-3-cyano-4,5,6,7-tetrahydro-benzo[b]thiophen-2-yl)-phthalamic acid,
2) N-(3-cyano-4,5,6,7-tetrahydro-benzo[b]thiophen-2-yl)-butyramide,
3) N-(3-cyano-4,5,6,7-tetrahydro-benzo[b]thiophen-2-yl)-3-nitro-benzamide,
4) N-(3-cyano-4,5,6,7-tetrahydro-benzo[b]thiophen-2-yl)-3,5-dinitro-benzamide,
5) 3-(3-cyano-4,5,6,7-tetrahydro-benzo[b]thiophen-2-ylcarbamoyl)-pyrazine-2-carboxylic acid,
6) 2,4-dichloro-N-(3-cyano-4,5,6,7-tetrahydro-benzo[b]thiophen-2-yl)-benzamide,
7) 3-methoxy-naphthalene-2-carboxylic acid (3-cyano-4,5,6,7-tetrahydro-benzo[b]thiophen-2-yl)-amide,
8) N-(3-cyano-4,5,6,7-tetrahydro-benzo[b]thiophen-2-yl)-2-fluoro-benzamide,
9) biphenyl-4-carboxylic acid (3-cyano-4,5,6,7-tetrahydro-benzo[b]thiophen-2-yl)-amide, 10) N-(3-cyano-4,5,6,7-tetrahydro-benzo[b]thiophen-2-yl)-4-piperidine-1-sulfonyl)-benzamide,
11) N-(3-cyano-4,5,6,7-tetrahydro-benzo[b]thiophen-2-yl)-4-dipropylsulfamoyl-benzamide,
12) thiophene-2-carboxylic acid (3-cyano-4,5,6,7-tetrahydro-benzo[b]thiophen-2-yl)-amide,
13) 4-benzoyl-N-(3-cyano-4,5,6,7-tetrahydro-benzo[b]thiophen-2-yl)-benzamide,
14) 4-chloro-N-(3-cyano-4,5,6,7-tetrahydro-benzo[b]thiophen-2-yl)-3-nitro-benzamide,
15) N-(3-cyano-4,5,6,7-tetrahydro-benzo[b]thiophen-2-yl)-2-methyl-3-nitro-benzamide,
16) 4-acetyl-N-(3-cyano-4,5,6,7-tetrahydro-benzo[b]thiophen-2-yl)-benzamide,
17) N-(3-cyano-4,5,6,7-tetrahydro-benzo[b]thiophen-2-yl)-4-methyl-3-(piperidine-1-sulfonyl)-benzamide,
18) 2,4-dichloro-N-(3-cyano-4,5,6,7-tetrahydro-benzo[b]thiophen-2-yl)-5-(morpholine-4-sulfonyl)-benzamide,
19) N-(3-cyano-4,5,6,7-tetrahydro-benzo[b]thiophen-2-yl)-3-(morpholine-4-sulfonyl)-benzamide,
20) N-(3-cyano-4,5,6,7-tetrahydro-benzo[b]thiophen-2-yl)-3,4,5-trimethoxy-benzamide,
21) N-(3-cyano-4,5,6,7-tetrahydro-benzo[b]thiophen-2-yl)-3-diethylsulfomoyl-benzamide,
22) 5-phenyl-7-trifluoromethyl-pyrazolo[1,5-a]pyrimidine-2-carboxylic acid (3-cyano-4,5,6,7-tetrahydro-benzo[b]thiophen-2-yl)-amide,
23) 3-bromo-5-phenyl-7-trifluoromethyl-pyrazolo[1,5-a]pyrimidine-2-carboxylic acid (3-cyano-4,5,6,7-tetrahydro-benzo[b]thiophen-2-yl)-amide,
24) N-(3-cyano-4,5,6,7-tetrahydro-benzo[b]thiophen-2-yl)-2-(5-methyl-3-trifluoromethyl-pyrazol-1-yl)-acetamide,
25) N-(3-cyano-4,5,6,7-tetrahydro-benzo[b]thiophen-2-yl)-2-(3-nitro-[1,2,4]triazol-1-yl)-acetamide,
26) N-(3-cyano-4,5,6,7-tetrahydro-benzo[b]thiophen-2-yl)-2-(4-nitro-imidazol-1-yl)-acetamide,
27) 2-chloro-N-(3-cyano-4,5,6,7-tetrahydro-benzo[b]thiophen-2-yl)-4-nitro-benzamide,
28) 5-bromo-furan-2-carboxylic acid (3-cyano-4,5,6,7-tetrahydro-benzo[b]thiophen-2-yl)-amide,
29) 2-chloro-N-(3-cyano-4,5,6,7-tetrahydro-benzo[b]thiophen-2-yl)-4-nitro-benzamide,
30) 2-chloro-N-(3-cyano-4,5,6,7-tetrahydro-benzo[b]thiophen-2-yl)-nicotinamide,
31) 2,4-dichloro-(3-cyano-4,5,6,7-tetrahydro-benzo[b]thiophen-2-yl)-benzamide,
32) N-(6-tert-butyl-3-cyano-4,5,6,7-tetrahydro-benzo[b]thiophen-2-yl)-2-phenyl-2-phenylsulfanyl-acetamide,
33) N-(3-cyano-4,5,6,7-tetrahydro-benzo[b]thiophen-2-yl)-2-(1-phenyl-1H-tetrazol-5-ylsulfanyl)-acetamide,
34) 2-chloro-N-(3-cyano-4,5,6,7-tetrahydro-benzo[b]thiophen-2-yl)-5-(piperidine-1-sulfonyl)-benzamide,
35) 6-bromo-pyrazolo[1,5-a]pyrimidine-2-carboxylic acid (3-cyano-4,5,6,7-tetrahydro-benzo[b]thiophen-2-yl)-amide,
36) 3,6-dibromo-pyrazolo[1,5-a]pyrimidine-2-carboxylic acid (3-cyano-4,5,6,7-tetrahydro-benzo[b]thiophen-2-yl)-amide,
37) 4-tert-butyl-N-(3-cyano-4,5,6,7-tetrahydro-benzo[b]thiophen-2-yl)-benzamide,
38) 3-chloro-6-fluoro-benzo[b]thiophene-2-carboxylic acid (3-cyano-4,5,6,7-tetrahydro-benzo[b]thiophen-2-yl)-amide,
39) benzo[1,3]dioxole-5-carboxylic acid (3-cyano-4,5,6,7-tetrahydro-benzo[b]thiophen-2-yl)-amide,
40) N-(3-cyano-4,5,6,7-tetrahydro-benzo[b]thiophen-2-yl)-4-(2,4-dichloro-phenoxy)-butyramide,
41) N-(3-cyano-4,5,6,7-tetrahydro-benzo[b]thiophen-2-yl)-2-(4-methyl-piperazin-1-yl)-acetamide,
42) 2-phenyl-quinoline-4-carboxylic acid (3-cyano-4,5,6,7-tetrahydro-benzo[b]thiophen-2-yl)-amide,
43) pentanoic acid (3-cyano-4,5,6,7-tetrahydro-benzo[b]thiophen-2-yl)-amide,
44) 3-chloro-5-phenyl-7-trifluoromethyl-pyrazolo[1,5-a]pyrimidine-2-carboxylic acid (3-cyano-4,5,6,7-tetrahydro-benzo[b]thiophen-2-yl)-amide,
45) N-(3-cyano-4,5,6,7-tetrahydro-benzo[b]thiophen-2-yl)-3-fluoro-benzamide,
46) N-(3-cyano-4,5,6,7-tetrahydro-benzo[b]thiophen-2-yl)-3,4,5-triethoxy-benzamide,
47) N-(3-cyano-4,5,6,7-tetrahydro-benzo[b]thiophen-2-yl)-acetamide,
48) 2-bromo-N-(3-cyano-4,5,6,7-tetrahydro-benzo[b]thiophen-2-yl)-benzamide,
49) 2-chloro-N-(3-cyano-4,5,6,7-tetrahydro-benzo[b]thiophen-2-yl)-benzamide,
50) N-(3-cyano-4,5,6,7-tetrahydro-benzo[b]thiophen-2-yl)-4-nitro-benzamide,
51) 8-allyl-2-oxo-2H-chromene-3-carboxylic acid (3-cyano-4,5,6,7-tetrahydro-benzo[b]thiophen-2-yl)-amide,
52) N-(3-cyano-4,5,6,7-tetrahydro-benzo[b]thiophen-2-yl)-2,2-dimethyl-propionamide,
53) N-(3-cyano-4,5,6,7-tetrahydro-benzo[b]thiophen-2-yl)-4-methyl-benzamide,
54) N-(3-cyano-4,5,6,7-tetrahydro-benzo[b]thiophen-2-yl)-3-methoxy-benzamide,
55) 3-bromo-N-(3-cyano-4,5,6,7-tetrahydro-benzo[b]thiophen-2-yl)-benzamide,
56) 4-tert-butyl-N-(3-cyano-4,5,6,7-tetrahydro-benzo[b]thiophen-2-yl)-benzamide,
57) naphthalene-1-carboxylic acid (3-cyano-4,5,6,7-tetrahydro-benzo[b]thiophen-2-yl)-amide,
58) N-(3-cyano-4,5,6,7-tetrahydro-benzo[b]thiophen-2-yl)-3-phenoxy-benzamide,
59) N-(3-cyano-4,5,6,7-tetrahydro-benzo[b]thiophen-2-yl)-2-phenyl-acetamide,
60) 4-butoxy-N-(3-cyano-4,5,6,7-tetrahydro-benzo[b]thiophen-2-yl)-benzamide,
61) N-(3-cyano-4,5,6,7-tetrahydro-benzo[b]thiophen-2-yl)-4-morpholine-4-sulfonyl)-benzamide,
62) N-(3-cyano-4,5,6,7-tetrahydro-benzo[b]thiophen-2-yl)-2-methoxy-benzamide,
63) N-(3-cyano-4,5,6,7-tetrahydro-benzo[b]thiophen-2-yl)-2-nitro-benzamide,
64) N-(3-cyano-4,5,6,7-tetrahydro-benzo[b]thiophen-2-yl)-3-methyl-butyramide,
65) 2-(1,3-dioxo-1,3-dihydro-isoindol-2-yl)-4,5,6,7-tetrahydro-benzo[b]thiophene-3-carbonitrile,
66) N-(3-cyano-4,5,6,7-tetrahydro-benzo[b]thiophen-2-yl)-benzamide,
67) 4-(3-cyano-4,5,6,7-tetrahydro-benzo[b]thiophen-2-yl-carbamoyl)-butyric acid,
68) 4-bromo-N-(3-cyano-4,5,6,7-tetrahydro-benzo[b]thiophen-2-yl)-benzamide,
69) 4-chloro-N-(3-cyano-4,5,6,7-tetrahydro-benzo[b]thiophen-2-yl)-benzamide,
70) N-(3-cyano-4,5,6,7-tetrahydro-benzo[b]thiophen-2-yl)-2-(3,5-dimethyl-4-nitro-pyrazol-1-yl)-acetamide,
71) 2-(4-bromo-5-methyl-3-trifluoromethyl-pyrazol-1-yl)-N-(3-cyano-4,5,6,7-tetrahydro-benzo[b]thiophen-2-yl)-acetamide,
72) 5-(4-fluoro-phenyl)-7-trifluoromethyl-pyrazolo[1,5-a]pyrimidine-2-carboxylic acid (3-cyano-4,5,6,7-tetrahydro-benzo[b]thiophen-2-yl)-amide, 73) 5-phenyl-7-trifluoromethyl-pyrazolo[1,5-a]pyrimidine-2-carboxylic acid (6-tert-butyl-3-cyano-4,5,6,7-tetrahydro-benzo[b]thiophen-2-yl)-amide,
74) 5-phenyl-7-trifluoromethyl-pyrazolo[1,5-a]pyrimidine-2-carboxylic acid (3-cyano-4,5,6,7-tetrahydro-benzo[b]thiophen-2-yl)-amide,
75) 3-bromo-5-phenyl-7-trifluoromethyl-pyrazolo[1,5-a]pyrimidine-2-carboxylic acid (3-cyano-4,5,6,7-tetrahydro-benzo[b]thiophen-2-yl)-amide,
76) 5-furan-2-yl-7-trifluoromethyl-pyrazolo[1,5-a]pyrimidine-2-carboxylic acid (3-cyano-4,5,6,7-tetrahydro-benzo[b]thiophen-2-yl)-amide,
77) 5-furan-2-yl-7-trifluoromethyl-pyrazolo[1,5-a]pyrimidine-2-carboxylic acid (3-cyano-4,5,6,7-tetrahydro-benzo[b]thiophen-2-yl)-amide,
78) 3-bromo-5-thiophen-2-yl-7-trifluoromethyl-pyrazolo[1,5-a]pyrimidine-2-carboxylic acid (3-cyano-4,5,6,7-tetrahydro-benzo[b]thiophen-2-yl)-amide,
79) 5-thiophen-2-yl-7-trifluoromethyl-pyrazolo[1,5-a]pyrimidine-2-carboxylic acid (6-tert-butyl-3-cyano-4,5,6,7-tetrahydro-benzo[b]thiophen-2-yl)-amide,
80) N-(6-tert-butyl-3-cyano-4,5,6,7-tetrahydro-benzo[b]thiophen-2-yl)-2-(5-methyl-3-nitro-pyrazol-1-yl)-acetamide,
81) N-(3-cyano-4,5,6,7-tetrahydro-benzo[b]thiophen-2-yl)-2-(5-methyl-3-nitro-pyrazol-1-yl)-acetamide,
82) 2-(4-bromo-5-methyl-3-nitro-pyrazol-1-yl)-N-(6-tert-butyl-3-cyano-4,5,6,7-tetrahydro-benzo[b]thiophen-2-yl)-acetamide,
83) 2-(4-bromo-5-methyl-3-nitro-pyrazol-1-yl)-N-(3-cyano-4,5,6,7-tetrahydro-benzo[b]thiophen-2-yl)-acetamide,
84) N-(6-tert-butyl-3-cyano-4,5,6,7-tetrahydro-benzo[b]thiophen-2-yl)-2-(3,5-dimethyl-4-nitro-pyrazol-1-yl)-acetamide,
85) N-(3-cyano-4,5,6,7-tetrahydro-benzo[b]thiophen-2-yl)-2-(3,5-dimethyl-4-nitro-pyrazol-1-yl)-acetamide,
86) 2-(4-bromo-5-methyl-3-trifluoromethyl-pyrazol-1-yl)-N-(6-tert-butyl-3-cyano-4,5,6,7-tetrahydro-benzo[b]thiophen-2-yl)-acetamide,
87) 2-(4-bromo-5-methyl-3-trifluoromethyl-pyrazol-1-yl)-N-(3-cyano-6-methyl-4,5,6,7-tetrahydro-benzo[b]thiophen-2-yl)-acetamide,
88) N-(6-tert-butyl-3-cyano-4,5,6,7-tetrahydro-benzo[b]thiophen-2-yl)-2-(5-methyl-3-trifluoromethyl-pyrazol-1-yl)-acetamide,
89) 5-phenyl-7-trifluoromethyl-pyrazolo[1,5-a]pyrimidine-3-carboxylic acid (6-tert-butyl-3-cyano-4,5,6,7-tetrahydro-benzo[b]thiophen-2-yl)-amide,
90) 5-(4-bromo-phenyl-7-trifluoromethyl-pyrazolo[1,5-a]pyrimidine-2-carboxylic acid (3-cyano-4,5,6,7-tetrahydro-benzo[b]thiophen-2-yl)-amide,
91) N-(3-cyano-4,5,6,7-tetrahydro-benzo[b]thiophen-2-yl)-2-methyl-benzamide,
92) N-(3-cyano-4,5,6,7-tetrahydro-benzo[b]thiophen-2-yl)-3,4-difluoro-benzamide,
93) 4-chloro-N-(3-cyano-4,5,6,7-tetrahydro-benzo[b]thiophen-2-yl)-3-(morpholine-4-sulfonyl)-benzamide,
94) 4-bromo-N-(3-cyano-4,5,6,7-tetrahydro-benzo[b]thiophen-2-yl)-3-(morpholine-4-sulfonyl-benzamide),
95) 4-cyano-N-(3-cyano-4,5,6,7-tetrahydro-benzo[b]thiophen-2-yl)-benzamide,
96) N-(3-cyano-4,5,6,7-tetrahydro-benzo[b]thiophen-2-yl)-3,4-dimethoxy-benzamide,
97) 2-(benzo[4,5]thiazolo[2,3-c][1,2,4]triazol-3-ylsulfanyl)-N-(3-cyano-4,5,6,7-tetrahydro-benzo[b]thiophen-2-yl)-acetamide,
98) tetrahydro-furan-2-carboxylic acid [3-cyano-6-(1,1-dimethyl-propyl)-4,5,6,7-tetrahydro-benzo[b]thiophen-2-yl]-amide,
99) 2,5-dichloro-N-[3-cyano-6-(1,1-dimethyl-propyl)-4,5,6,7-tetrahydro-benzo[b]thiophen-2-yl]-benzamide,
100) 5-(4-ethoxy-phenyl)-7-methyl-pyrazolo[1,5-a]pyrimidine-2-carboxlic acid (3-cyano-4,5,6,7-tetrahydro-benzo[b]thiophen-2-yl)-amide,
101) N-(3-cyano-6-methyl-4,5,6,7-tetrahydro-benzo[b]thiophen-2-yl)-2-(5-methyl-3-trifluoromethyl-pyrazol-1-yl)-acetamide,
102) 5,7-diphenyl-pyrazolo[1,5-a]pyrimidine-3-carboxylic acid (3-cyano-4,5,6,7-tetrahydro-benzo[b]thiophen-2-yl)-amide,
103) 2-(4-chloro-5-methyl-3-trifluoromethyl-pyrazol-1-yl)-N-(3-cyano-4,5,6,7-tetrahydro-benzo[b]thiophen-2-yl)-acetamide,
104) 3-chloro-N-(3-cyano-4,5,6,7-tetrahydro-benzo[b]thiophen-2-yl)-benzamide,
105) N-(3-cyano-4,5,6,7-tetrahydro-benzo[b]thiophen-2-yl)-3-nitro-phthalamic acid,
106) N-(3-cyano-5-methyl-4,5,6,7-tetrahydro-benzo[b]thiophen-2-yl)-propionamide,
107) N-(3-cyano-5-methyl-4,5,6,7-tetrahydro-benzo[b]thiophen-2-yl)-4-methoxy-benzamide,
108) N-(3-cyano-5-methyl-4,5,6,7-tetrahydro-benzo[b]thiophen-2-yl)-2-nitro-benzamide,
109) N-(3-cyano-5-methyl-4,5,6,7-tetrahydro-benzo[b]thiophen-2-yl)-4-ethoxy-benzamide,
110) N-(3-cyano-4,5,6,7-tetrahydro-benzo[b]thiophen-2-yl)-3,5-dimethoxy-benzamide,
111) N-(3-cyano-5-methyl-4,5,6,7-tetrahydro-benzo[b]thiophen-2-yl)-2,6-difluoro-benzamide,
112) N-(3-cyano-5-methyl-4,5,6,7-tetrahydro-benzo[b]thiophen-2-yl)-3-trifluoromethyl-benzamide,
113) 2-(4-chloro-phenoxy)-N-(3-cyano-5-methyl-4,5,6,7-tetrahydro-benzo[b]thiophen-2-yl)-acetamide, and
114) N-(3-cyano-5-methyl-4,5,6,7-tetrahydro-benzo[b]thiophen-2-yl)-2-phenoxy-acetamide.

In an additional embodiment, a chemical that has been identified as a cell migration inhibitor has a general formula of:

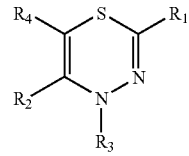

which is an organic molecule having a molecular weight of less than about 700. $R_1$ is selected from the group consisting of 4-bromo-benzoylamino, (adamantan-2-yl-hydroxy-methyl)-amino, and phenylamino. $R_2$ is selected from the group consisting of dihydro-benzo[1,4]dioxin-6-yl, p-chloro-phenyl, p-methyl-phenyl, phenyl, and p-methoxy-phenyl. $R_3$ is selected from the group consisting of hydrogen, 2-propenyl, and phenyl. $R_4$ is selected from the group consisting of hydrogen and methyl. In one embodiment, the chemical is [5-(2,3-dihydro-benzo[1,4]dioxin-6-yl)-4H-[1,3,4]thiadiazin-2-yl]-phenyl-amine.

Additional examples of chemicals having the above general formula that may exhibit cell migration inhibition include, but are not limited to:

1) N-[4-allyl-5-(4-chloro-phenyl)-6-methyl-4H-[1,3,4]thiadiazin-2-yl]-3-bromo-benzamide,
2) adamantan-1-yl-(4-allyl-5-p-tolyl-4H-[1,3,4]thiadiazin-2-ylamino)-methanol,
3) N-(4-allyl-5-phenyl-4H-[1,3,4]thiadiazin-2-yl)-4-bromo-benzamide,
4) N-[4-allyl-5-(4-chloro-phenyl)-6-methyl-4H-[1,3,4]thiadiazin-2-yl]-4-bromo-benzamide,
5) [5-(4-methoxy-phenyl)-4-phenyl-4H-[1,3,4]thiadiazin-2-yl]-phenyl-amine,
6) N-[4-allyl-5-(2,3-dihydro-benzo[1,4]dioxin-6-yl)-4H-[1,3,4]thiadiazin-2-yl]-3-bromo-benzamide, and
7) N-(4-allyl-5-phenyl-4H-[1,3,4]thiadiazin-2-yl)-3-bromo-benzamide.

The compounds described herein are arylating agents. Therefore, other relatively small organic molecules that are arylating agents may also exhibit cell migration. An embodiment of a method for inhibiting cell migration may include treating cells with one or more cell migration inhibitors that are arylating agents. In alternative embodiments, other compounds such as monoclonal antibodies, etc. may also exhibit cell migration. In one such embodiment, a method for inhibiting cell migration may include treating cells with one or more cell migration inhibitors that are monoclonal antibodies.

All of the chemicals described above are commercially available. For example, the chemicals are commercially available from Nanoscale Combinatorial Synthesis, Inc., Menlo Park, Calif.

The methods described herein may also be used to identify chemicals that inhibit angiogenesis. Angiogenesis inhibition involves reducing the development of new blood vessels. Cancer tumors induce the formation of new blood vessels to provide the nutritional needs of the tumor such that tumor growth can occur. In this manner, tumors grow or spread by developing new blood vessels. Angiogenesis is also related to metastasis. For example, tumors with higher densities of blood vessels are generally more likely to metastasize and are likely to have poorer outcomes. In addition, angiogenesis and metastasis need matrix metallaproteinases, which are enzymes that break down surrounding tissue (the extracellular matrix), during blood vessel and tumor invasion. Therefore, by inhibiting angiogenesis, the growth and spread of tumors to other parts of the body may be inhibited.

An embodiment of a chemical that has been identified as an angiogenesis inhibitor has a general formula of:

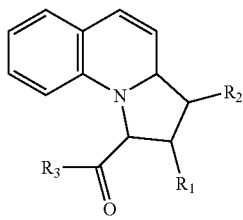

where $R_1$, $R_2$, and $R_3$ include the groups described herein for this general formula.

An additional embodiment of a chemical that has been identified as an angiogenesis inhibitor has a general formula of:

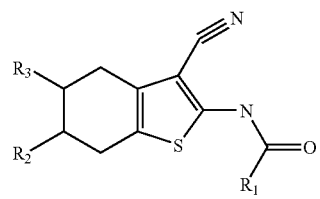

where $R_1$, $R_2$, and $R_3$ include the groups described herein for this general formula.

Another embodiment of a chemical that has been identified as an angiogenesis inhibitor has a general formula of:

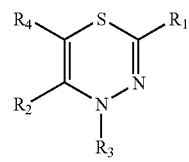

where $R_1$, $R_2$, $R_3$, and $R_4$ include the groups described herein for this general formula.

Figure 4A:
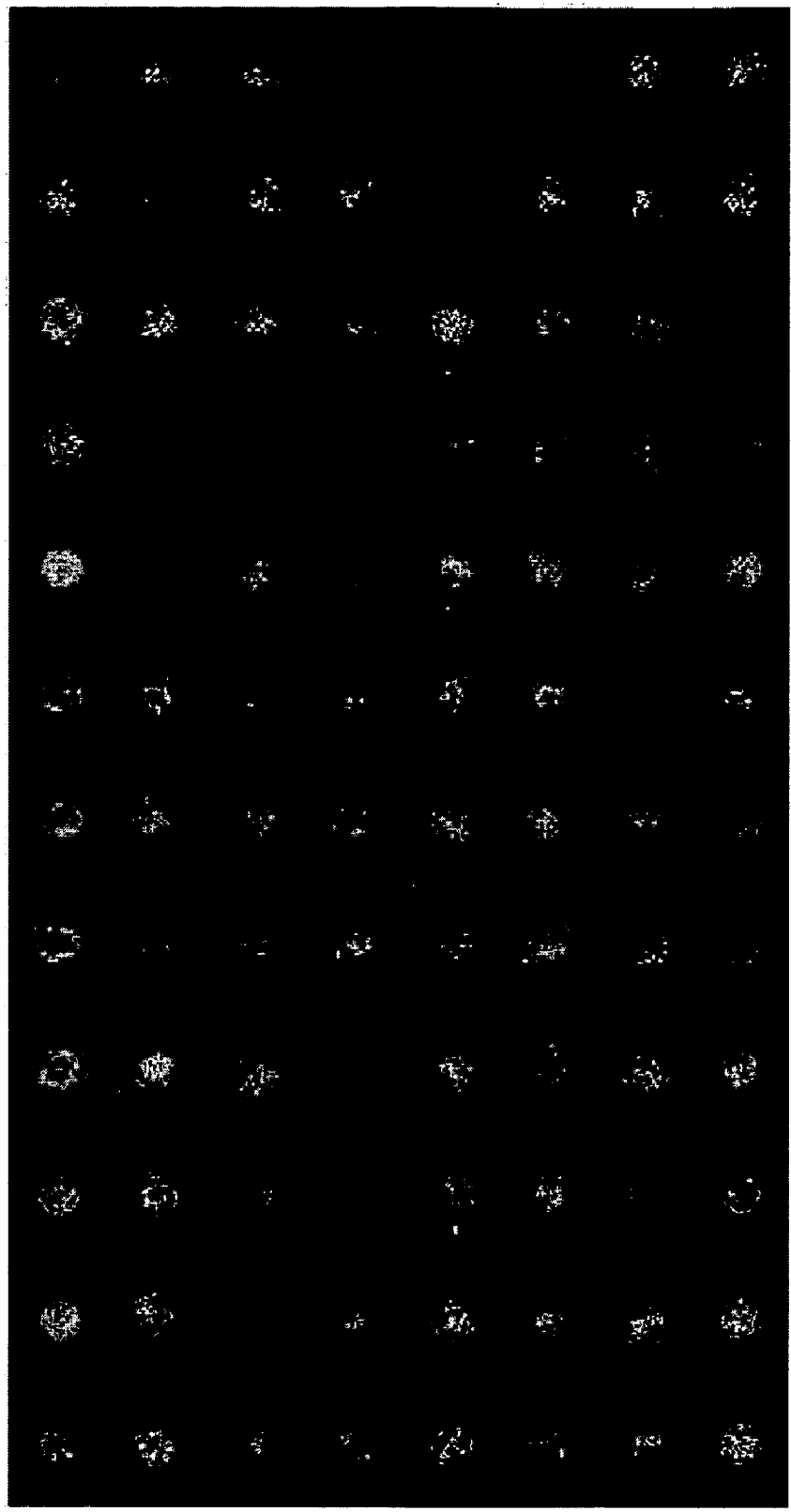
FIG. 4a is a top plan view of an example of a 96 well plate on which cancer cells were treated with different chemicals and allowed to migrate for a period of time.

In an embodiment, as shown in step 42 of FIG. 4, the method described above may include determining if a combination of a chemical that exhibits cell migration inhibition and a chemotherapeutic agent exhibit synergistic killing of cancer cells. Measuring the synergy of a combination of a chemical and a chemotherapeutic agent may be performed by the following method. A monolayer of cancer cells may be harvested using any method known in the art. A 96 well plate as described above is coated with a migration-induced substrate. Aliquot a volume of about 200 µl per well into each well or about 1000 cells per well. The perimeter wells of the plate are not used for cells, but are filled with sterile water to provide humidity control for the plate. The cells are allowed to sediment and attach to the wells by allowing the plate to sit for several hours or overnight. The cells are treated with doses of cell migration inhibiting chemicals in combination with a chemotherapeutic agent for a period of time (i.e., about 3, 4, or 5 days). After treatment, the cells are incubated with Alamar blue (about 10% volume/volume, or 20 µl in 200 µl). The cells are incubated at about 37° C. for about 4 hours. The amount of time that the cells are incubated may vary depending upon the type of cells that are being examined. The plate may be read on a microplate reader fluorometer, which has an excitation of about 530 nm and an emission of about 590 nm. The results are based on changes in absorbance (cell number) as a function of drug treatment. FIG. 4*a* illustrates a top plan view of an example of a 96 well plate on which cancer cells were treated with different chemicals and allowed to migrate for a period of time. As shown in FIG. 4*a*, the absorbance measured in each well varies depending upon drug treatment. A cell dilution plate should be run to generate a standard curve. The data is analyzed by subtracting a blank from all of the absorbance measurements. The mean values are reported as fractional absorbance of each of the means from treated wells relative to the control well. Statistical tests can be performed for replicate measurements.

Measuring the synergy of a combination of a chemical and a chemotherapeutic agent may also be performed by evaluating the growth inhibitory effects of a chemotherapeutic agent and a cell migration inhibitor in a severe combined immunodeficient (scid) mouse human tumor model. Such measurements include screening mice for immunoglobulin (Ig) production by an enzyme-linked immunosorbent assay (ELISA). A number of mice are injected with cancer cells in saline using a subcutaneous (SC) injection. Mice with established tumors are selected and stratified according to groups including: a control group, a group treated with a chemotherapeutic agent alone, a group treated with a cell migration inhibitor alone, and one or more groups treated with various combinations of the chemotherapeutic agent and the cell migration inhibitor. The groups designated to be treated with at least the chemotherapeutic agent are injected with the chemotherapeutic agent or the chemotherapeutic agent diluent by intraperitoneal (IP, within abdominal cavity) injection on the first day of treatment. In some cancer models, these groups may also be injected with the chemotherapeutic agent or the chemotherapeutic agent diluent by IP injection every other day (qod) about 5 times (qod×5). The groups designated to be treated with at least the cell migration inhibitor are injected with the cell migration inhibitor or the cell migration inhibitor diluent by EP injection qod×5. Tumor growth may be measured about twice a week throughout the experiment, and the tumor volume may be estimated using the following formula: $[(\text{width})^2 \times \text{length}]/2$. The mice are weighed before the beginning of the experiment and once a week thereafter to check for signs of toxicity.

The methods described above may be used to identify anti-invasive and anti-metastatic agents. In other words, the methods may be used to identify chemicals that will reduce the transmission of disease from one original site to one or more sites elsewhere in the body. In addition, although chemotherapeutic agents are the standard therapy for metastatic cancer treatments, currently available chemotherapeutic agents have several limitations. For example, when cancer cell migrate, the cells undergo few cellular processes and markedly reduced cell division. Such reduced cell division renders them relatively insensitive to chemotherapeutic agents, which attack and kill dividing cells. Therefore, inhibition of cell migration may lead to cell death and to increased sensitivity to chemotherapy agents.

Cell migration inhibition, therefore, may be used as a portion of cancer treatment based on initial inhibition of cell migration followed by treatment with chemotherapeutic agents and optionally radiation. In this manner, an embodiment of a method for treating an individual having cancer includes administering a cell migration inhibitor and a chemotherapeutic agent to the individual to inhibit migration of cancer cells. The cell migration inhibitor may include any of the cell migration inhibitors described herein. For example, the cell migration inhibitor may include an organic molecule having a molecular weight of less than about 700, a monoclonal antibody, or a natural product. Inhibiting cell migration initiates many cellular processes including increasing cell division, which is the target of most chemotherapy. Therefore, the cell migration inhibitor and the chemotherapeutic agent in combination has increased efficacy compared to the chemotherapeutic agent alone due to the increased cell division.

In addition, the amount of chemotherapeutic agents and optionally radiation used in combination with a cell migration inhibitor for cancer treatments may be lower than an amount of chemotherapeutic agents or radiation used alone for treating cancer. Furthermore, reducing the amount of chemotherapeutic agents or radiation used for cancer treatments will reduce the adverse events that an individual being treated with chemotherapeutic agents or radiation for cancer may experience. Examples of adverse events of chemotherapeutic agents include, but are not limited to, neutropenia, thrombocytopenia, anemia, infection, febrile neutropenia, septic death, nonseptic death, acute hypersensitivity, fluid retention, neurosensory, myalgia, cutaneous, asthenia, diarrhea, and stomatitis. An appropriate dosage of a combination of a cell migration inhibitor and a chemotherapeutic agent may be determined by any method known in the art. For example, results of animal studies using the cell migration inhibitor and a chemotherapeutic agent may be used to determine an appropriate dosage for human clinical studies and ultimately for treatment.

An embodiment of a pharmaceutical composition includes any of the cell migration inhibitors described herein and a chemotherapeutic agent. The pharmaceutical composition may also include more than one of the cell migration inhibitors described herein and/or more than one chemotherapeutic agents. The pharmaceutical composition also includes a pharmaceutically acceptable carrier. The carrier may include any known pharmaceutically acceptable carrier that is compatible with the cell migration inhibitor, the chemotherapeutic agent, and any other components of the composition. The carrier should also not be deleterious to the recipient. The pharmaceutical composition may be formed such that the composition may be administered to an individual in any manner known in the art (i.e., orally, intravenously, etc.).

Another embodiment relates to a pharmaceutical composition that includes one or more cell migration inhibitors, of which at least one is an arylating agent, and one or more chemotherapeutic agents. The chemotherapeutic agents may include any chemotherapeutic agents known in the art. The pharmaceutical composition may also include a pharmaceutically acceptable carrier as described above.

Examples of appropriate chemotherapeutic agents that may be combined with any of the cell migration inhibitors described herein include, but are not limited to, an alkylaing agent, an antitumor agent, an antimetabolite, an antineoplastic agent, an antimicrotubule agent, a spindle-tubule inhibitor, a topoisomerase inhibitor, a hormonal agent, a biological agent, and a granulocyte-colony stimulating factor. Appropriate chemotherapeutic agents may also include any other chemotherapeutic agents known in the art or currently approved chemotherapeutic agents and optionally radiation. In one embodiment, a pharmaceutical composition includes the cell migration inhibitor 4'-propyl-bicyclohexyl-4-carboxylic acid and the chemotherapeutic agent 1,3-bis(2-chloroethyl)-1-nitrosourea (BCNU). In other embodiments, a pharmaceutical composition includes the cell migration inhibitor 4-methyl-3-nitro-benzoic acid and BCNU or paclitaxel. Another embodiment of a pharmaceutical composition includes the cell migration inhibitor 1-(4-chloro-benzoyl)-2-(3,4-dimethoxy-phenyl)-1,2-dihydro-3aH-pyrrolo[1,2-a]quinoline-3,3-dicarbonitrile and gemcytabine. An additional embodiment of a pharmaceutical composition includes the cell migration inhibitor 1-(4-chloro-benzoyl)-2-(4-methoxy-phenyl)-1,2-dihydro-3aH-pyrrolo[1,2-a]quinoline-3,3-dicarbonitrile and gemcytabine.

A chemotherapy agent, as used herein, generally refers to a cytotoxic agent. Cytotoxic agents generally exhibit selective toxicity based on characteristics that distinguish malignant cells from normal cells. Cytotoxic agents also generally exhibit antineoplastic effects such as cell death, cell growth inhibition, and cell differentiation. Haskell C M. *Cancer Treatment.* 4$^{th}$ ed. 1995; 32. Cytotoxic opportunities in a cell cycle generally occur after the $G_2$ period or cell division and at the beginning of the $G_1$ period or the (chromosome replication) s-phase. Each type of chemotherapeutic agent may include several classes of cytotoxic agents and has a different mechanism for killing cells.

There are several classes of alkylating agents. For example, alkylating agents include nitrogen mustards (i.e., cyclophosphamide, melphalan), arizidines (e.g., thiotepa), alkyl alkone sulfonates (i.e., busulfan), nitrosoureas (i.e., carmustine), non-classic alkylating agents (i.e., procarbazine), and platinum compounds (i.e., carboplatin, cisplatin). Examples of commercially available alkylating agents include, for example, Paraplatin® Injection (carboplatin) and Platinol®-AQ Injection (cisplatin), which are available from Bristol Myers Squibb Oncology/Immunology Division/A Bristol Myers Squibb Company, Princeton, N.J. Alkylating agents are generally polyfunctional compounds that cause cytotoxicity by alkylation of guanine and interference with DNA replication/transcription to RNA. Alkylating agents are cell-cycle-phase nonspecific. Gerson S L. *Current Cancer Therapeutics*. $3^{rd}$ ed. 1998; 1.

Antitumor antibiotics include anthracyclines (i.e., doxorubicin, daunorubicin, epirubicin, idarubicin), anthracenedione (i.e., mitoxantrone), mitomycin C, bleomycin, dactinomycin, and plicamycin. Blum R H. *Current Cancer Therapeutics*. $3^{rd}$ ed. 1998; 37-40. Examples of commercially available antitumor antibiotics include Doxil®, which is commercially available from Sequus Pharmaceuticals, Menlo Park, Calif. Antitumor antibiotics are generally polyfunctional agents that bind directly to DNA thereby causing uncoiling or breakage of the helix and impairment of DNA and RNA synthesis. Antitumor antibiotics may also have other cytotoxic mechanisms such as free-radical formation, chelation of important metals, and inhibition of topoisomerase II. Blum R H. *Current Cancer Therapeutics*. $3^{rd}$ ed. 1998; 35, 37.

Classes of antimetabolites include antifols (i.e., methotrexate), purine analogs (i.e., thiguanine, pentostatin, and cladribine), and pyrimidine analogs (i.e., fluorouracil, cytarabine, gemcitabine). Chiao J, et al. *Current Cancer Therapeutics*. $3^{rd}$ ed. 1998; 50-66. Antimetabolites generally cause cytoxicity by replacing metabolites in key DNA/RNA replication molecules, thereby impairing functionality, competing with metabolites at catalytic sites of key enzymes, and/or competing with metabolites at regulatory sites of key enzymes. Haskell C M. *Current Cancer Therapeutics*. $3^{rd}$ ed. 1998; 36. Examples of commercially available antimetabolites include Gemzar® commercially available from Eli Lilly and Company, Indianapolis, Ind.

Spindle-tubule inhibitors include vinca alkaloids (i.e., vincristine, vinblastine, vinorelbine) and taxanes. Agarwala S S. *Current Cancer Therapeutics*. $3^{rd}$ ed. 1998; 105-122. Topoisomerase inhibitors include podophyllotoxin derivatives (i.e., etoposide, teniposide) and camptothecin derivatives (i.e., topotecan, irinotecan). Agarwala S S. *Current Cancer Therapeutics*. $3^{rd}$ ed. 1998; 105.

Categories of hormonal agents include additive (i.e., estrogen, progestins, androgens), ablative (i.e., ovariectomy, orchiectomy), competitive (i.e., antiestrogens, antiprogestins, antiandrogens), and inhibitive (i.e., aromatase inhibitors, lutenizing hormon-releasing hormone (LH-RH) analogs). Kiang D T. *Current Cancer Therapeutics*. $3^{rd}$ ed. 1998; 88-90. Hormonal agents generally cause cytotoxicity by modulating activity of hormones on nuclear or cytoplasmic receptors and subsequent induction of mRNA synthesis and/or protein synthesis changes in cell functioning. Haskell C M. *Cancer Treatment*. $3^{rd}$ ed. 1995; 31-51. Examples of hormonal agents include megestrol acetate for advanced breast and endometrial cancers, tamoxifen for breast cancer and in combination for other cancers such as melanoma, LH-RH agonists in combination with flutamide for androgen blockage in prostate cancer, and prednisone as part of a combination therapy for Hodgkin's disease, non-Hodgkin's lymphoma, myeloma, and acute lymphoblastic leukemia. Prednisone may also be used as a palliative therapy for breast and prostate cancer. Kian D T. *Current Cancer Therapeutics*. $3^{rd}$ ed. 1998; 88-104 and Haskell C M. *Cancer Treatment*. 4th ed. 1995; 85-165. Examples of commercially available hormonal agents include Nolvadex® (tamoxiphen) available from AstraZeneca Pharmaceuticals, L.P., Wilmington, Del. Hormonal therapies are frequently used for the palliative treatment of hormone dependent cancers such as breast, prostate, and endometrial cancer. Hormonal therapies are often preferred over the more toxic chemo- and radiotherapies.

Other cytotoxic agents include biological agents such as cytokines (i.e., interleukin-2, interferon alpha, colony stimulating factors), immunomodulating reagents (i.e., bacillus Calmette-Guérin, levamisole), and octapeptide (i.e, octreotide). Baar J, et al. *Current Cancer Therapeutics*. $3^{rd}$ ed. 1998; 67-76. In addition, cytotoxic agents include granulocyte-colony stimulating factor (G-SCF). G-SCFs are produced normally by mononuclear phagocytes, endothelial cells, fibroblasts, and neutrophils. G-CSF acts to control the number of circulating blood neutrophils, improves neutropenia and reduces infection in sold-tumor patients receiving myelosuppressive therapy. Baar J, et al. *Current Cancer Therapeutics*. $3^{rd}$ ed. 1998; 71-72.

Antimicrotubule agents generally cause cytotoxicity by promoting assembly of microtubules and stabilizes microtubules by inhibiting depolymerization. Examples of antimicrotubule agents include paclitaxil, which is commercially available as Taxol® from Bristol Myers Squibb, and docetaxel, which is commercially available as Taxotere® from Aventis Pharmaceuticals Products Inc., Bridgewater, N.J.

Methods for treating an individual having cancer are also provided. In an embodiment, treating an individual having cancer include administering a cell migration inhibitor and a chemotherapeutic agent to the individual. The cell migration inhibitor may include any of the cell migration inhibitors described herein, and the chemotherapeutic agent may include any of the chemotherapeutic agents described herein or known in the art. In addition, the cell migration inhibitor and the chemotherapeutic agent may be administered in a pharmaceutical composition, which may be configured as described above. An additional embodiment relates to a method for treating an individual having cancer that includes administering a cell migration inhibitor that is an arylating agent and a chemotherapeutic agent to the individual. The method may be carried out as described herein.

The types of cancers that can be treated using the methods described herein include, but are not limited to, glioma (brain cancer), breast cancer, breast cancer with metastasis to the brain, lung/bronchus cancer, lung cancer with metastasis to the brain, melanoma (skin cancer), melanoma with metastasis to the brain, other central nervous system cancer, pancreatic cancer, stomach cancer, liver cancer, colon/rectum cancer, cervix uteri cancer, corpus uteri cancer, ovarian cancer, prostate cancer, bladder cancer, mouth/pharynx cancer, esophagus cancer, leukemia, and Non-Hodgkin's lymphoma.

A method for treating a disease, which is at least partially attributable to abnormal cell migration, is also provided. The disease may be, but is not limited to, autoimmune disease and cardiovascular disease. The method includes altering abnormal cell migration of the disease by administering a cell migration inhibitor to an individual having the disease. The cell migration inhibitor may include any of the cell migration inhibitors described herein. The method also includes treating the disease by administering a pharmaceutical agent to the individual. The pharmaceutical agent may include any pharmaceutical agent appropriate for treatment of the disease.

Figure 5:
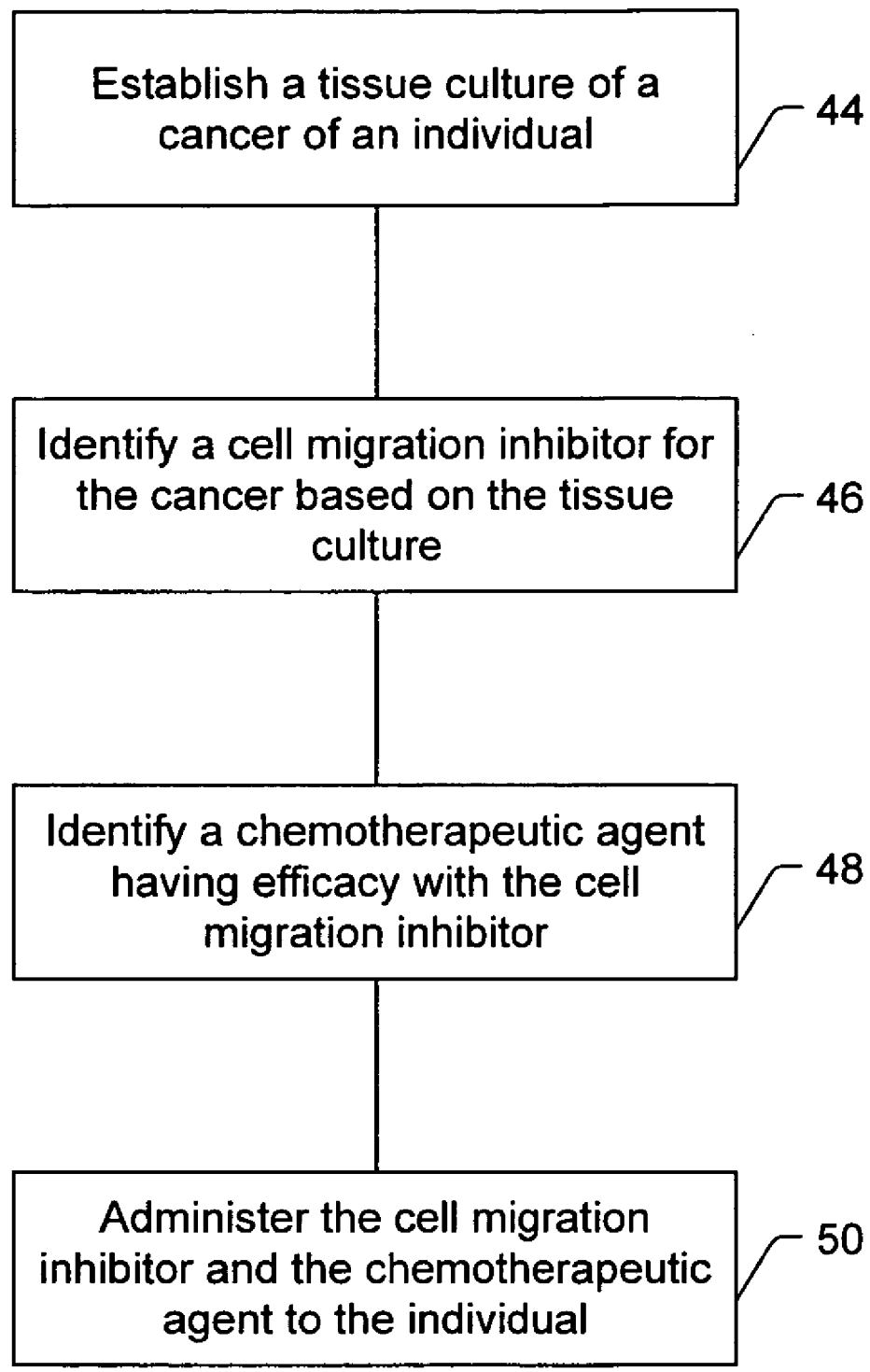
FIG. 5 is a flow chart illustrating an embodiment of a method for identifying a treatment for an individual having cancer.

FIG. 5 is a flow chart illustrating a method for identifying a treatment for an individual having cancer. As shown in step 44, the method may include establishing a tissue culture of the cancer of the individual. The tissue culture may be established using any method known in the art. The method may also include identifying a cell migration inhibitor for the cancer based on the tissue culture, as shown in step 46. The methods described above may be used to screen a relatively large number of potential cell migration inhibitors in a relatively short amount of time. Therefore, a cell migration rate of cells from the tissue culture can be measured with a number of potential cell migration inhibitors. A cell migration inhibitor appropriate for treatment of the individual may be selected from among the screened chemicals, and optionally a dose response curve may be generated. In addition, the method may include identifying a chemotherapeutic agent that has efficacy in combination with the cell migration inhibitor, as shown in step 48. Such identification may be performed using high throughput screening of cells from the tissue culture treated with the identified cell migration inhibitor and a number of chemotherapeutic agents as described herein. The chemotherapeutic agents may include any chemotherapeutic agent described herein. As shown in step 50, the method may include administering the cell migration inhibitor and the chemotherapeutic agent to the individual as described above.

Example 1

Screening a Library of Chemicals for Cell Migration Inhibition

Figure 6:
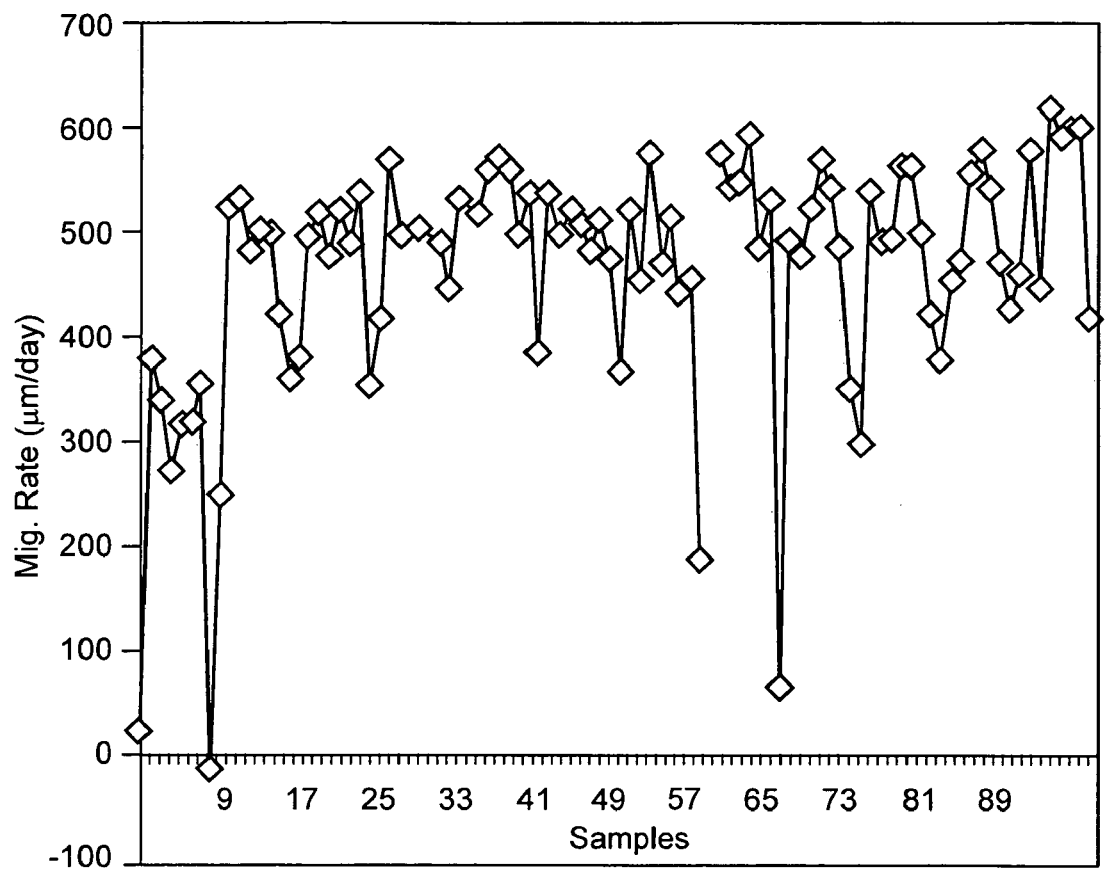
FIG. 6 is a plot illustrating results of a screening experiment using chemicals selected from a library and cancer cells.

FIG. 6 is a plot illustrating results of a screening experiment using chemicals selected from a library and cancer cells. The screening experiment was carried out as described above. The cancer cells used in the experiment are glioma cancer cells. Cell migration of cancer cells was measured in the presence of chemicals selected from the library. The cell migration was measured as described above and is shown on the y-axis in units of μm/day. The samples are shown on the x-axis, and the chemicals or untreated control samples are indicated by well number. As shown in FIG. 6, a plurality of chemicals from the library were screened and several of the chemicals shown markedly reduced migration in comparison to untreated control samples of the cancer cells and most of the treatment wells. For example, chemicals in wells labeled 1, 8, 58, and 66 show markedly reduced migration in comparison to the untreated and other treated samples.

Example 2

Dose Response Curve of Glioma Cancer Cells to a Cell Migration Inhibitor

Figure 7:
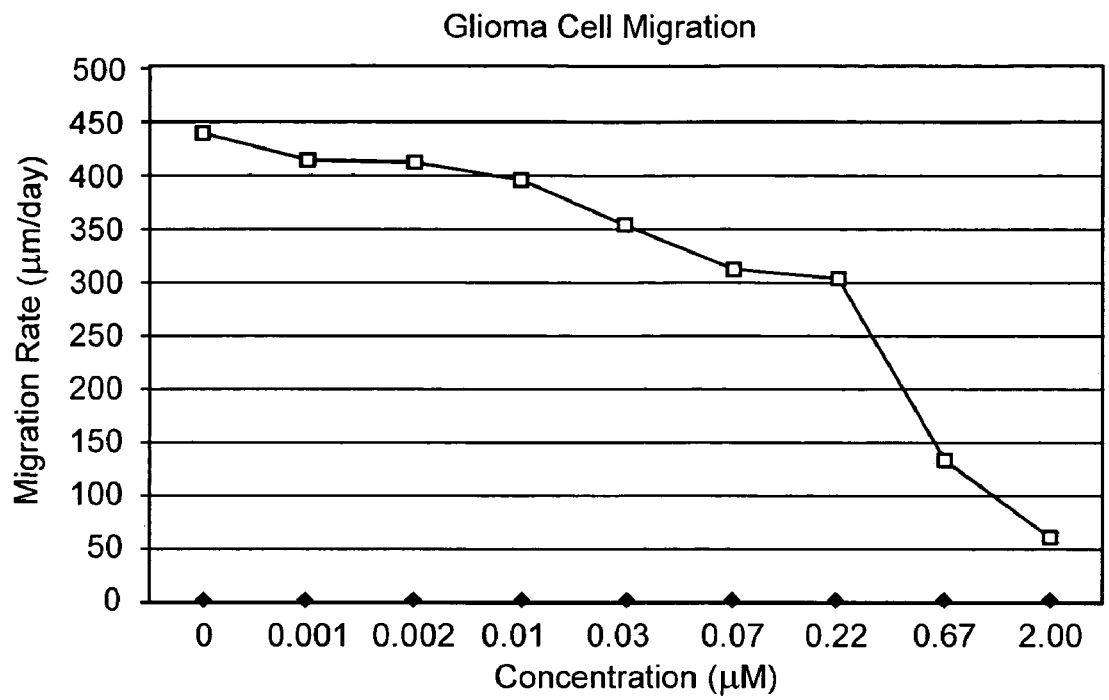
FIG. 7 is a plot illustrating cell migration rate of glioma cancer cells as a function of concentration of 4'-propyl-bicyclohexyl-4-carboxylic acid.

FIG. 7 is a plot illustrating cell migration rate, in units of μm/day, as a function of concentration of 4'-propyl-bicyclohexyl-4-carboxylic acid, in units of μM. This chemical was selected from a plurality of chemicals from a library because cancer cells treated with the chemical had a lower cell migration rate than untreated cancer cells. Therefore, several samples of glioma cancer cells were treated with various concentrations of the chemical. The glioma cancer cell line is SF 767. The concentration was varied from 0.000 μM to 2.00 μM of 4'-propyl-bicyclohexyl-4-carboxylic acid. The cell migration rate of each sample of the cancer cells was measured as described above. The dose-response curve shown in FIG. 7 illustrates the measurement results. As shown in FIG. 7, the cell migration rate decreased from almost 450 μm/day at a concentration of 0.000 μM to about 50 μm/day at a concentration of 2.00 μM. Therefore, 4'-propyl-bicyclohexyl-4-carboxylic acid was identified as a glioma cancer cell migration inhibiting chemical.

Example 3

Synergy of a Cell Migration Inhibitor and a Chemotherapeutic Agent

Figure 8:
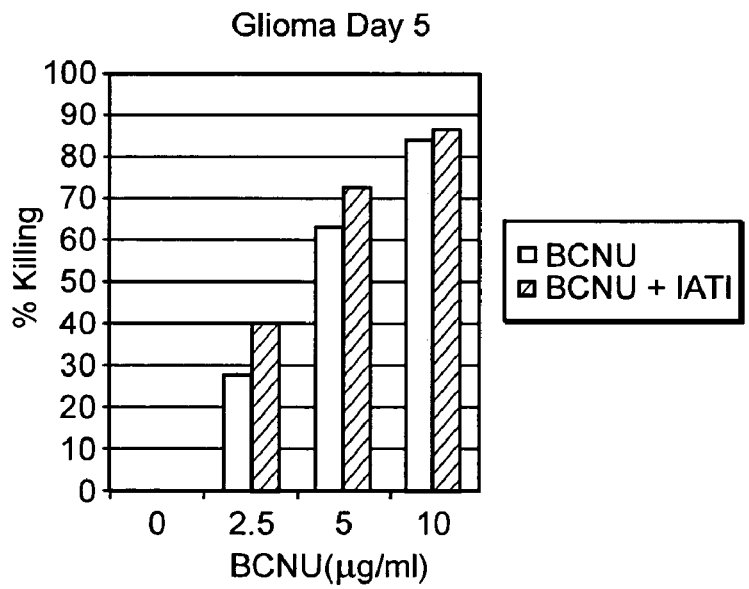
FIG. 8 is a bar graph illustrating % killing of glioma cancer cells as a function of concentration of BCNU and BCNU in combination with 4'-propyl-bicyclohexyl-4-carboxylic acid.

FIG. 8 is a bar graph illustrating % killing of cancer cells, in units of % dead cells, as a function of concentration of a chemotherapeutic agent and a chemotherapeutic agent in combination with a cell migration inhibitor, in units of μg/ml. The glioma cancer cell line is SF 767, which is described above. The chemotherapeutic agent is 1,3-bis(2-chloroethyl)-1-nitrosourea (BCNU), which is a currently approved chemotherapeutic agent commercially available from Bristol Myers Squibb. The cell migration inhibitor is 4'-propyl-bicyclohexyl-4-carboxylic acid. The killing of glioma cancer cells using BCNU and a combination of BCNU and 4'-propyl-bicyclohexyl-4-carboxylic acid was measured five days after initial treatment. As shown in FIG. 8, the combination of BCNU and 4'-propyl-bicyclohexyl-4-carboxylic acid exhibits higher killing percentages than BCNU alone. Therefore, the combination of BCNU and 4'-propyl-bicyclohexyl-4-carboxylic acid exhibits synergistic killing of glioma cancer cells. In addition, killing of glioma cancer cells using the combination of BCNU and 4'-propyl-bicyclohexyl-4-carboxylic acid is significantly higher than BCNU alone at low concentrations of BCNU. As such, a pharmaceutical composition of the combination of BCNU and 4'-propyl-bicyclohexyl-4-carboxylic acid may have a lower concentration of BCNU than a pharmaceutical composition that includes BCNU but not 4'-propyl-bicyclohexyl-4-carboxylic acid.

Example 4

Dose Response Curve of Breast Cancer Cells to a Cell Migration Inhibitor

Figure 9:
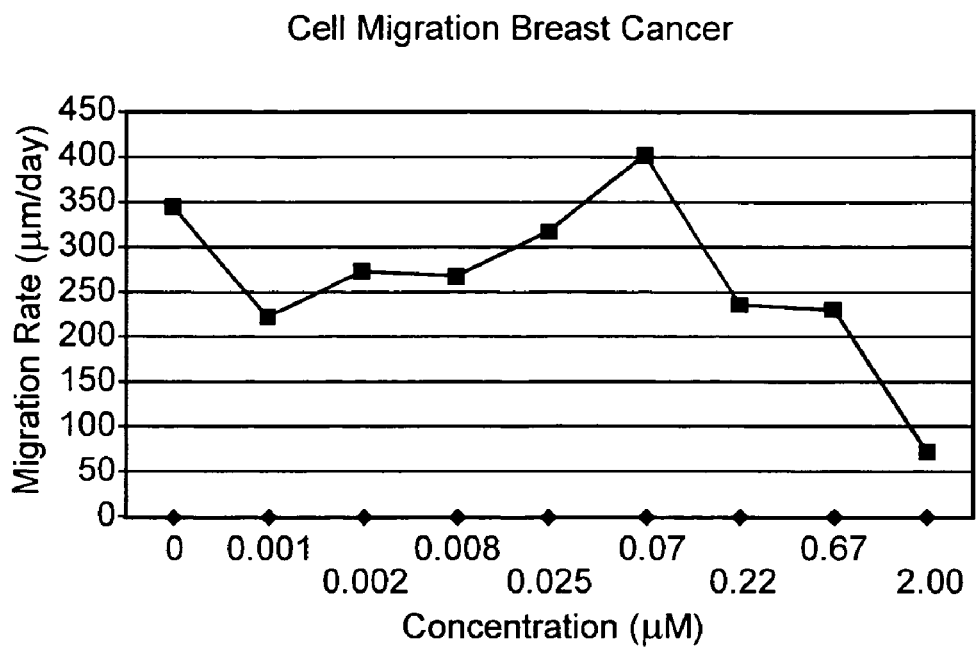
FIG. 9 is a plot illustrating cell migration rate of breast cancer cells as a function of concentration of 4-methyl-3-nitro-benzoic acid.

FIG. 9 is a plot illustrating cell migration rate, in units of μm/day, as a function of concentration of 4-methyl-3-nitro-benzoic acid, in units of μM. This chemical was selected from a plurality of chemicals from a library because cancer cells treated with the chemical had a lower cell migration rate than untreated cancer cells. Therefore, several samples of breast cancer cells were treated with various concentrations of the chemical. The breast cancer cell line is MDA-MB-231, which is a cell line characterized as human, Caucasian, breast, adenocarcinoma. Such a cell line is available from several cell line catalogues and from several labs such as CAMR Centre for Applied Microbiology and Research, Salisbury, Wiltshire, Instituto Nazionale per la Ricerca Sul Cancro, Genova, and Dip. Scienze Biomediche ed Oncologia Umana, Torino. The concentration was varied from 0.000 μM to 2.00 μM of 4-methyl-3-nitro-benzoic acid. The cell migration rate of each sample of the cancer cells was measured as described above. The dose-response curve shown in FIG. 9 illustrates the measurement results. As shown in FIG. 9, the cell migration rate decreased from greater than 350 μm/day at a concentration of 0.000 μM to about 75 μm/day at a concentration of 2.00 μM.

Therefore, 4-methyl-3-nitro-benzoic acid was identified as a breast cancer cell migration inhibiting chemical.

Example 5

Synergy of a Cell Migration Inhibitor and a Chemotherapeutic Agent

Figure 10:
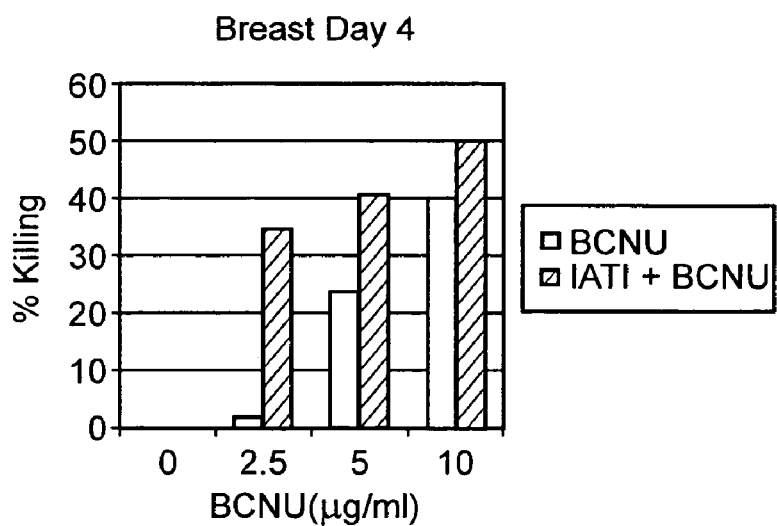
FIG. 10 is a bar graph illustrating % killing of breast cancer cells as a function of concentration of BCNU and BCNU in combination with 4-methyl-3-nitro-benzoic acid.

FIG. 10 is a bar graph illustrating % killing of cancer cells, in units of % dead cells, as a function of concentration of a chemotherapeutic agent and a chemotherapeutic agent in combination with a cell migration inhibitor, in units of μg/ml. The breast cancer cell line is MDA-MB-231, which is described above. The chemotherapeutic agent is BCNU. The cell migration inhibitor is 4-methyl-3-nitro-benzoic acid, which is labeled in the plot as IATI. The killing of breast cancer cells using BCNU and a combination of BCNU and 4-methyl-3-nitro-benzoic acid was measured four days after initial treatment. As shown in FIG. 10, the combination of BCNU and 4-methyl-3-nitro-benzoic acid exhibits higher killing percentages than BCNU alone. Therefore, the combination of BCNU and 4-methyl-3-nitro-benzoic acid exhibits synergistic killing of breast cancer cells. In addition, killing of breast cancer cells using the combination of BCNU and 4-methyl-3-nitro-benzoic acid is significantly higher than BCNU at low concentrations of BCNU. As such, a pharmaceutical composition of the combination of BCNU and 4-methyl-3-nitro-benzoic acid may have a lower concentration of BCNU than a pharmaceutical composition that includes BCNU but not 4-methyl-3-nitro-benzoic acid.

Example 6

Figure 11:
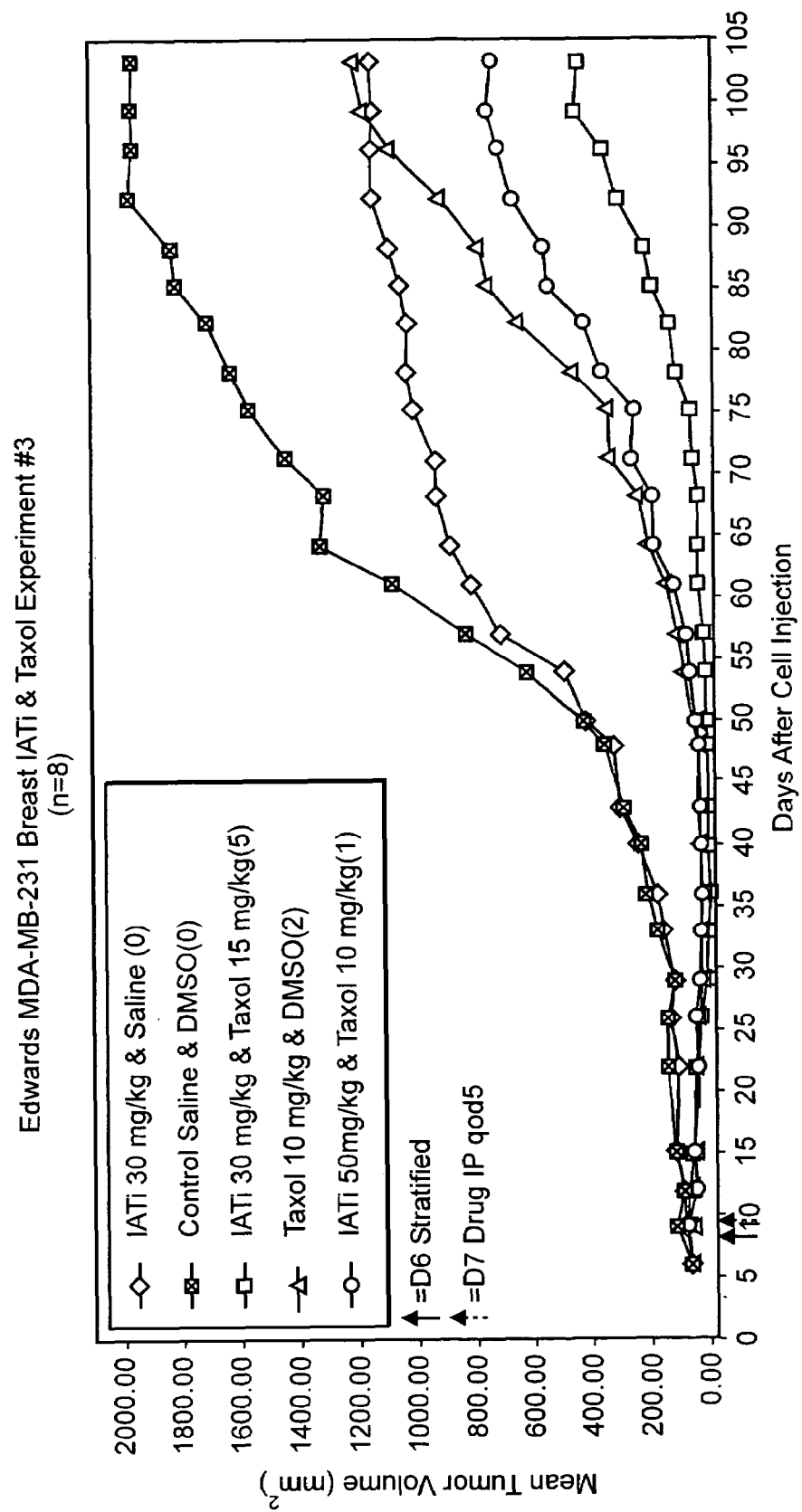
FIG. 11 is a plot illustrating mean tumor volume of breast cancer tumors as a function of time after cell injection of various pharmaceutical compositions.

Tumor Growth Inhibition Using a Pharmaceutical Composition Including a Cell Migration Inhibitor and a Chemotherapeutic Agent FIG. 11 is a plot illustrating mean tumor volume, in units of $mm^3$, as a function of time after cell injection of various pharmaceutical compositions, in units of days. The scid mouse human breast tumor model was used to evaluated cancer cells of the cell line MDA-MB-231 treated with various compositions. The various pharmaceutical compositions include a cell migration inhibitor alone, a chemotherapeutic agent alone, and various combinations of a cell migration inhibitor and a chemotherapeutic agent. The cell migration inhibitor is 4-methyl-3-nitro-benzoic acid, which is labeled in the plot as IATI. The chemotherapeutic agent is Taxol, which is a currently approved chemotherapeutic agent commercially available from Bristol Myers Squibb Oncology/Immunology Division/A Bristol Myers Squibb Company, Princeton, N.J.

The experiment was carried out as described above. 40 female scid mice were screened for immunoglobulin production by ELISA. 40 scid mice were injected with $10 \times 10^6$ MDA-MB-231 breast cancer cells in matrigel using a SC injection. 40 mice with established tumors (about 60 $mm^3$ to about 100 $mm^3$) were selected and stratified on day 6. Each of the animals in the treatment groups received IP injections qod×5 of one of the pharmaceutical compositions starting on day 6. Control animals, or untreated animals, were injected with a solution of DMSO and saline. Treated animals were injected with saline and 30 mg/kg of 4-methyl-3-nitro-benzoic acid, DMSO and 10 mg/kg of Taxol, a combination of 15 mg/kg of Taxol and 30 mg/kg of 4-methyl-3-nitro-benzoic acid, or a combination of 10 mg/kg of Taxol and 50 mg/kg of 4-methyl-3-nitro-benzoic acid.

As shown in FIG. 11, after 100 days, control animals had a mean tumor volume of about 2500 $mm^3$. Animals treated with Taxol alone or 4-methyl-3-nitro-benzoic acid alone had a mean tumor volume of slightly less than 1000 $mm^3$. In contrast, animals injected with the combination of 10 mg/kg of Taxol and 50 mg/kg of 4-methyl-3-nitro-benzoic acid had tumors that had a mean tumor volume of less than about 600 $mm^3$, while animals injected with the combination of 15 mg/kg of Taxol and 30 mg/kg of 4-methyl-3-nitro-benzoic acid had tumors that had a mean tumor volume of less than about 300 $mm^3$. Therefore, the combination of Taxol and 4-methyl-3-nitro-benzoic acid exhibits significant synergistic inhibition of breast cancer tumor growth. In addition, the concentrations of Taxol and 4-methyl-3-nitro-benzoic acid in a pharmaceutical composition may be altered to vary the mean tumor growth.

Figure 12:
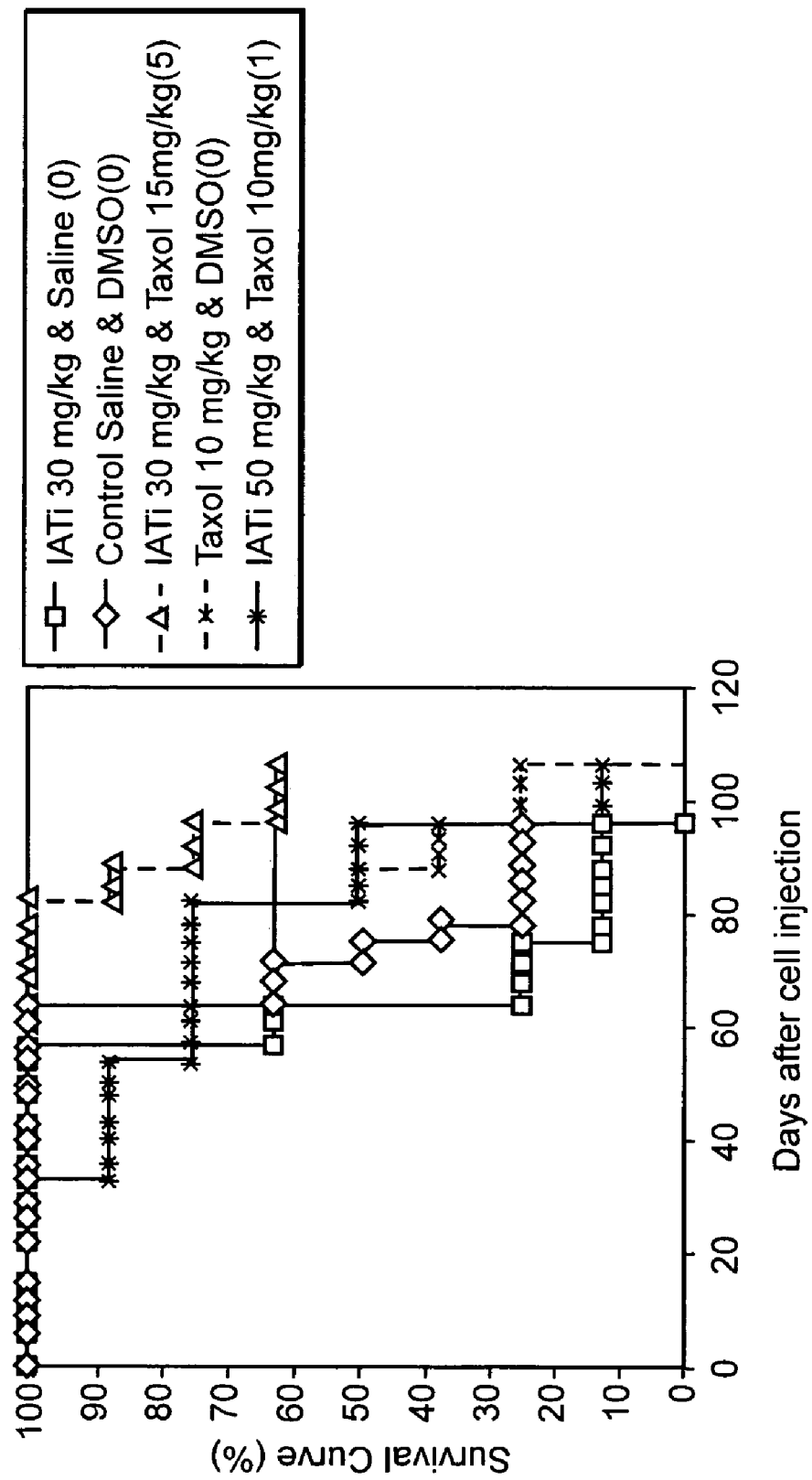
FIG. 12 is a plot illustrating percent survival of the mice used in the experiment of FIG. 11 as a function of time after days after cell injection.

FIG. 12 is a plot illustrating percent survival of the mice used in the above experiment, in units of %, as a function of days after cell injection. As shown in FIG. 12, mice treated with a combination of 15 mg/kg of Taxol and 30 mg/kg of 4-methyl-3-nitro-benzoic acid had the highest survival percentage throughout the time period of the experiment. In addition, even 100 days after injection, over 60% of these mice were still alive. Furthermore, mice treated with a combination of 10 mg/kg of Taxol and 50 mg/kg of 4-methyl-3-nitro-benzoic acid or Taxol alone had better survival percentages than the mice treated with 4-methyl-3-nitro-benzoic acid alone and the control mice. Table 1 is a summary of the survival of the mice used in the above study after 100 days of treatment.

TABLE 1

| Treatment | % Survival after 100 days |
| --- | --- |
| Control | 0 |
| 4-methyl-3-nitro-benzoic acid | 0 |
| Taxol | 0 |
| 30 mg/kg of 4-methyl-3-nitro-benzoic acid and 15 mg/kg of Taxol | 62.5 |
| 50 mg/kg of 4-methyl-3-nitro-benzoic acid and 10 mg/kg of Taxol | 12.5 |

Example 7

Dose Response Curve of Melanoma Cancer Cells to a Cell Migration Inhibitor

Figure 13:
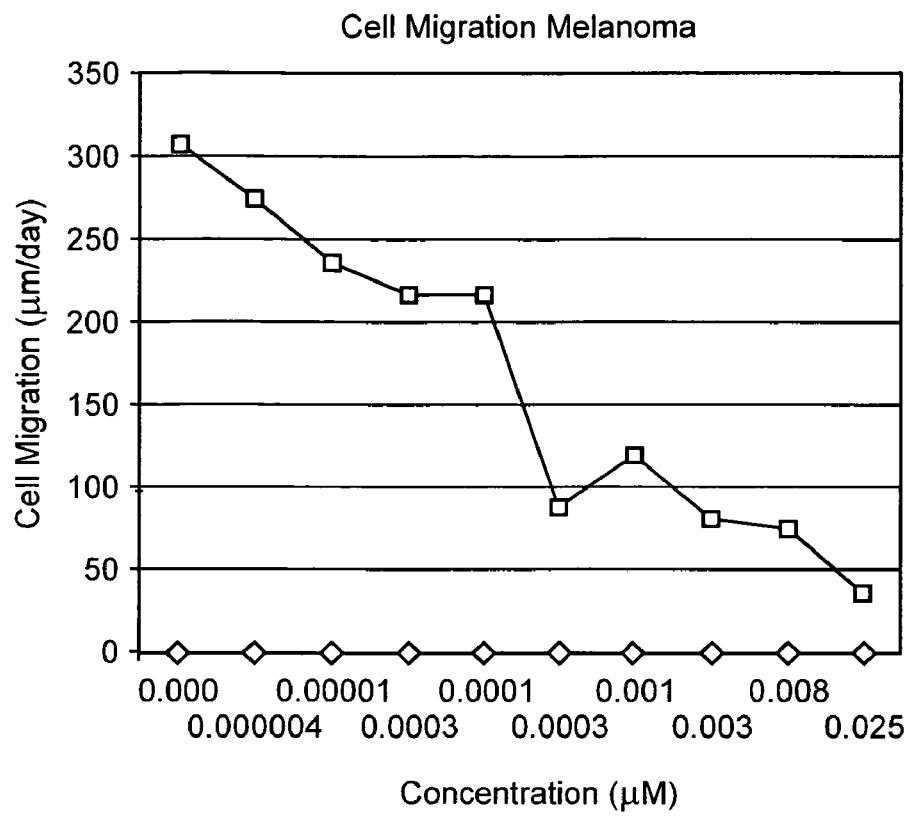
FIG. 13 is a plot illustrating cell migration rate of melanoma cancer cells as a function of concentration of 4-methyl-3-nitro-benzoic acid.

FIG. 13 is a plot illustrating cell migration rate, in units of μm/day, as a function of concentration of 4-methyl-3-nitro-benzoic acid, in units of μM. This chemical was selected from a plurality of chemicals from a library because cancer cells treated with the chemical had a lower cell migration rate than untreated cancer cells. Therefore, several samples of melanoma cancer cells were treated with various concentrations of the chemical. The melanoma cancer cell line is WM1791C. The concentration was varied from 0.000 μM to 0.025 μM of 4-methyl-3-nitro-benzoic acid. The cell migration rate of each sample of the cancer cells was measured. The dose-response curve shown in FIG. 13 illustrates the measurement results. As shown in FIG. 13, the cell migration rate decreased from greater than 300 μM/day at a concentration of 0.000 μM to less than 50 μM/day at a concentration of 0.025 μM. Therefore, 4-methyl-3-nitro-benzoic acid was identified as a melanoma cancer cell migration inhibiting chemical.

Example 8

Synergy of a Cell Migration Inhibitor and a Chemotherapeutic Agent

Figure 14:
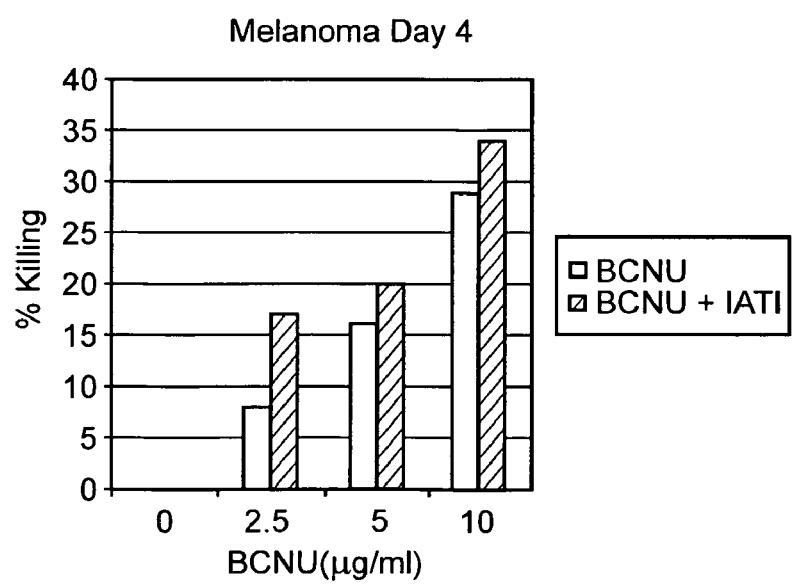
FIG. 14 is a bar graph illustrating % killing of melanoma cancer cells as a function of concentration of BCNU and BCNU in combination with 4-methyl-3-nitro-benzoic acid.

FIG. 14 is a bar graph illustrating % killing of cancer cells, in units of % dead cells, as a function of concentration of a chemotherapeutic agent and a chemotherapeutic agent in combination with a cell migration inhibitor, in units of μg/ml. The melanoma cancer cell line is WM1791C. The chemotherapeutic agent is BCNU. The cell migration inhibitor is 4-methyl-3-nitro-benzoic acid. The killing of melanoma cancer cells using BCNU and a combination of BCNU and 4-methyl-3-nitro-benzoic acid was measured four days after initial treatment. As shown in FIG. 14, the combination of BCNU and 4-methyl-3-nitro-benzoic acid exhibits higher killing percentages than BCNU alone. Therefore, the combination of BCNU and 4-methyl-3-nitro-benzoic acid exhibits synergistic killing of melanoma cancer cells. In addition, killing of melanoma cancer cells using the combination of BCNU and 4-methyl-3-nitro-benzoic acid increases as the concentration of BCNU is decreased. As such, a pharmaceutical composition of the combination of BCNU and 4-methyl-3-nitro-benzoic acid may have a lower concentration of BCNU than a pharmaceutical composition that includes BCNU but not 4-methyl-3-nitro-benzoic acid.

Example 9

Figure 15:
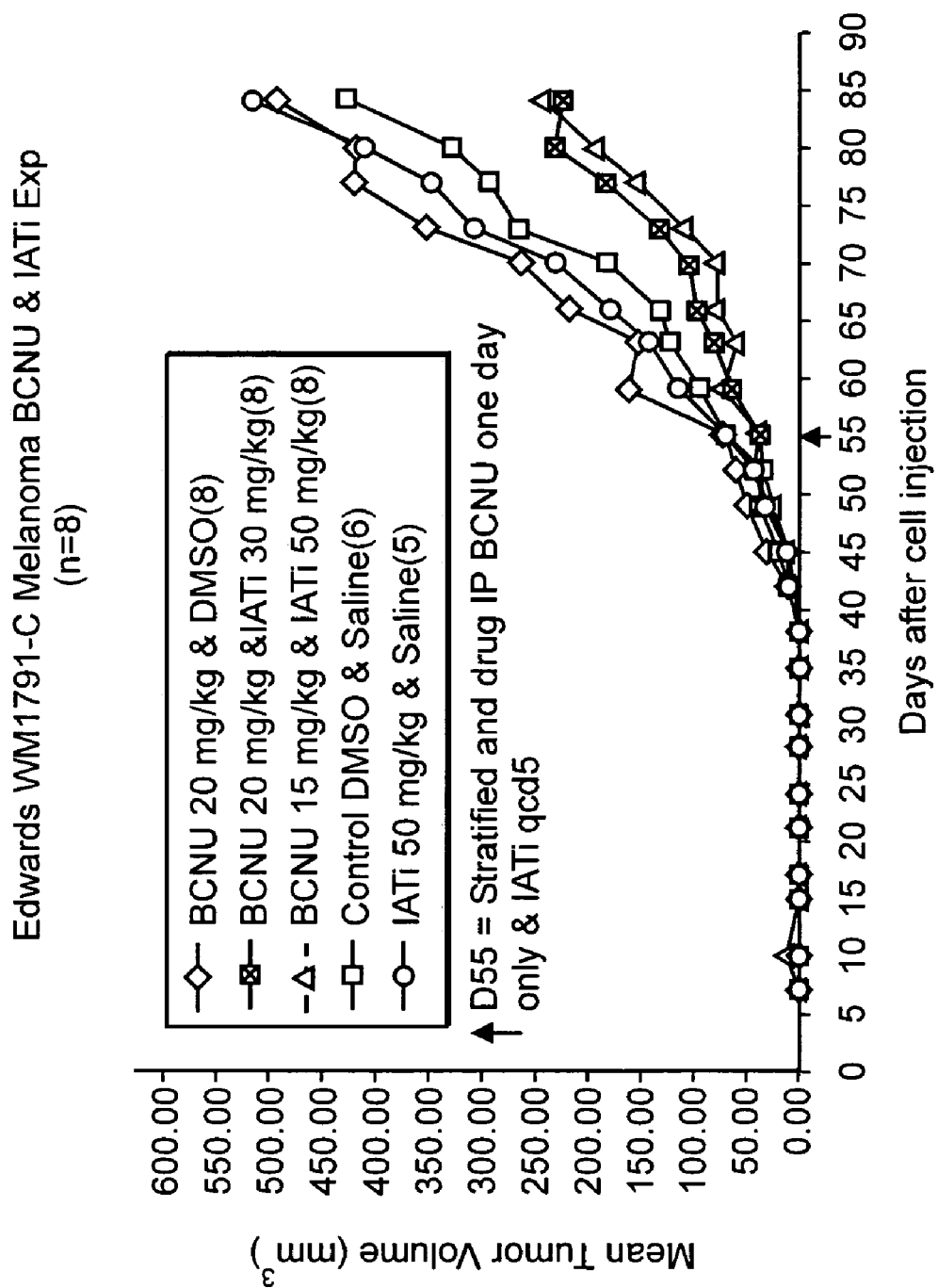
FIG. 15 is a plot illustrating mean tumor volume of melanoma tumors as a function of time after cell injection of various pharmaceutical compositions.

Tumor Growth Inhibition Using a Pharmaceutical Composition Including a Cell Migration Inhibitor and a Chemotherapeutic Agent FIG. 15 is a plot illustrating mean tumor volume, in units of $mm^3$, as a function of time after cell injection of various pharmaceutical compositions, in units of days. This In-Vitro animal model of melanoma cancer includes treating cancer cells of the cell line WM1791-C (also called UACC 1791C) with various pharmaceutical compositions and a control composition of DMSO and saline. The various pharmaceutical compositions include a cell migration inhibitor alone, a chemotherapeutic agent alone, and various combination of a cell migration inhibitor and a chemotherapeutic agent. The cell migration inhibitor is 4-methyl-3-nitro-benzoic acid, which is labeled in the plot as IATI. The chemotherapeutic agent is BCNU.

The animals used in the study were scid mice, and the experiment was carried out as described above. 40 scid mice were screened for immunoglobulin (Ig) production by ELISA. 40 mice were inoculated with $10 \times 10^6$ WM1791C melanoma cancers cells in saline using a SC injection. Animals with established tumors were stratified on day 55. Different groups of animals were treated with 50 mg/kg of 4-methyl-3-nitro-benzoic acid and saline, 20 mg/kg of BCNU and DMSO, a combination of 15 mg/kg of BCNU and 50 mg/kg of 4-methyl-3-nitro-benzoic acid, or combination of 20 mg/kg of BCNU and 30 mg/kg of 4-methyl-3-nitro-benzoic acid. Each of the animals designated to be treated with at least BCNU received IP injections of BCNU or BCNU diluent on day 55. Animals designated to be treated with at least 4-methyl-3-nitro-benzoic acid received IP injections of the cell migration inhibitor or the cell migration inhibitor diluent qod×5. The tumor growth was measured and the tumor volume was estimated as described above. Mice were also weight before the beginning of the experiment and once a week thereafter to check for signs of toxicity.

As shown in FIG. 15, even after 80 days, animals injected with either one of the combinations of BCNU and 4-methyl-3-nitro-benzoic acid had tumors that were less than about 250 $mm^3$, while all other animals had tumors that were greater than 400 $mm^3$. Therefore, the combination of BCNU and 4-methyl-3-nitro-benzoic acid exhibits synergistic inhibition of melanoma cancer tumor growth.

Example 10

Cell Migration Inhibition of Lung Cancer Cells

Figure 16:
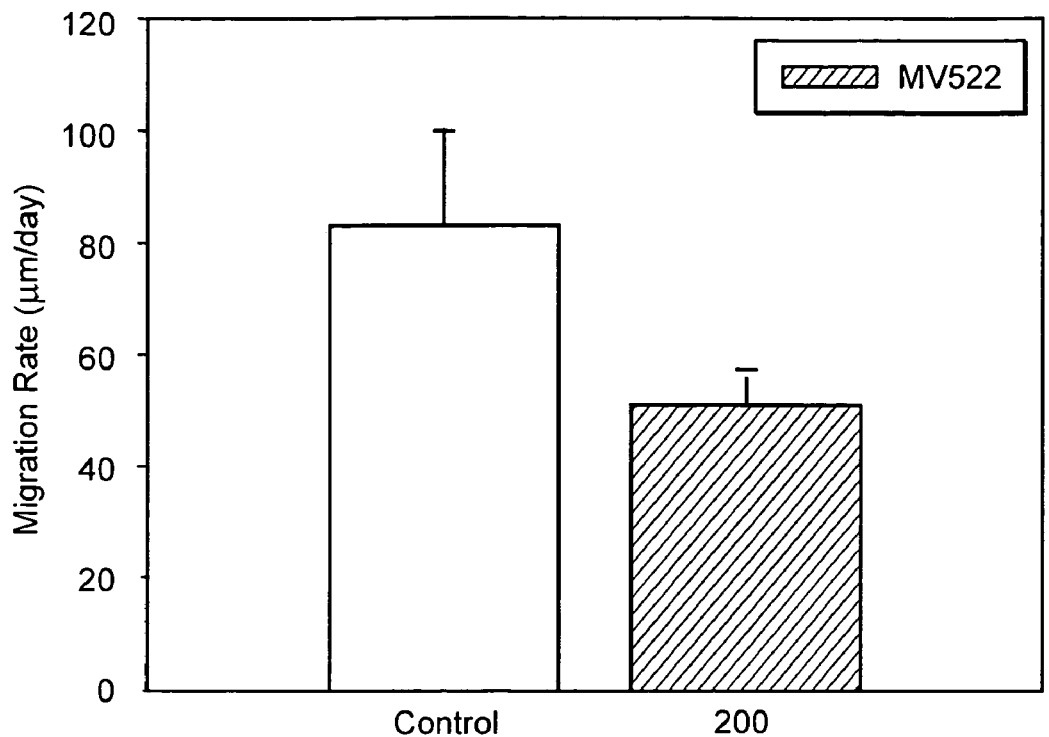
FIG. 16 is a bar graph illustrating cell migration rate for an untreated sample of lung cancer cells and a treated sample of lung cancer cells.

FIG. 16 is a bar graph illustrating cell migration rate, in units of μm/day, for an untreated sample of lung cancer cells and a treated sample of lung cancer cells. The lung cancer cell line is MV522. The control sample is the untreated cancer cells. The treated sample was treated with a chemical selected from a library of chemicals having a formula of: 4-methyl-3-nitro-benzoic acid. As shown in FIG. 16, the lung cancer cells treated with 4-methyl-3-nitro-benzoic acid show markedly reduced migration in comparison to the untreated control sample. Therefore, 4-methyl-3-nitro-benzoic acid has been identified as a cell migration inhibiting chemical.

Example 11

Cell Migration Inhibition of Pancreatic Cancer Cells

Figure 17:
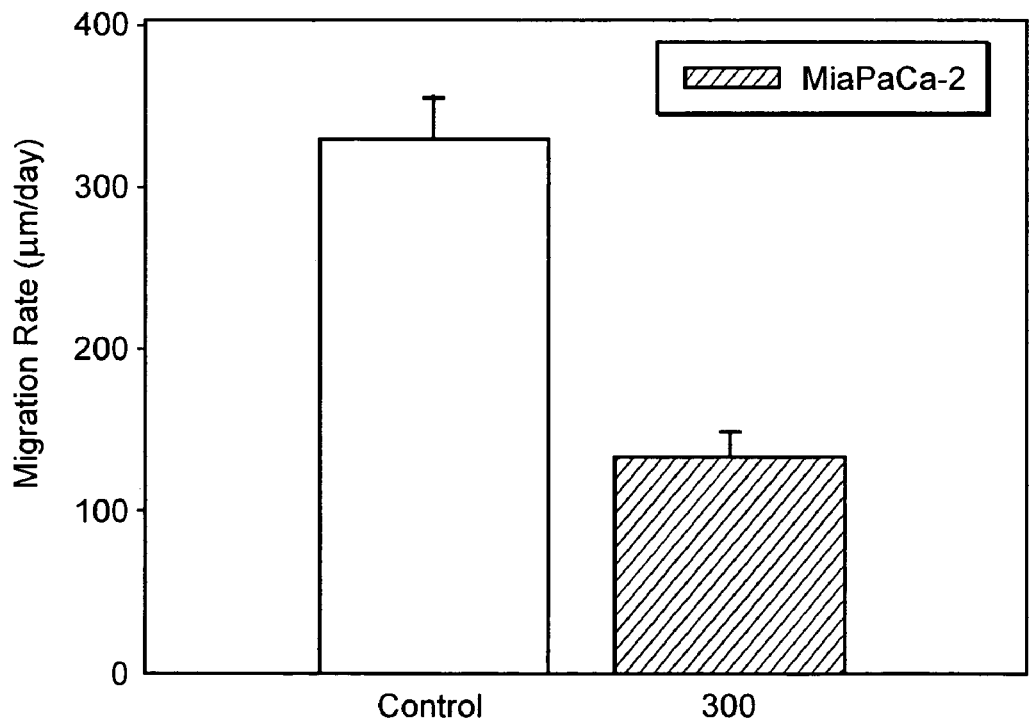
FIG. 17 is a bar graph illustrating cell migration rate for an untreated sample of pancreatic cancer cells and a treated sample of pancreatic cancer cells.

FIG. 17 is a bar graph illustrating cell migration rate, in units of μm/day for an untreated sample of pancreatic cancer cells and a treated sample of pancreatic cancer cells. The pancreatic cancer cell line is MiaPaCa-2. The control sample is the untreated cancer cells. The treated sample was treated with a chemical selected from a library of chemicals having a formula of: 1-(4-chloro-benzoyl)-2-(3,4-dimethoxy-phenyl)-1,2-dihydro-3aH-pyrrolo[1,2-a]quinoline-3,3-dibarbonitrile. As shown in FIG. 17, the pancreatic cancer cells treated with 1-(4-chloro-benzoyl)-2-(3,4-dimethoxy-phenyl)-1,2-dihydro-3aH-pyrrolo[1,2-a]quinoline-3,3-dicarbonitrile show markedly reduced migration in comparison to the untreated control sample. Therefore, 1-(4-chloro-benzoyl)-2-(3,4-dimethoxy-phenyl)-1,2-dihydro-3aH-pyrrolo[1,2-a]quinoline-3,3-dicarbonitrile has been identified as a cell migration inhibiting chemical.

Example 12

Cell Migration Inhibition of Pancreatic Cancer Cells

Figure 18:
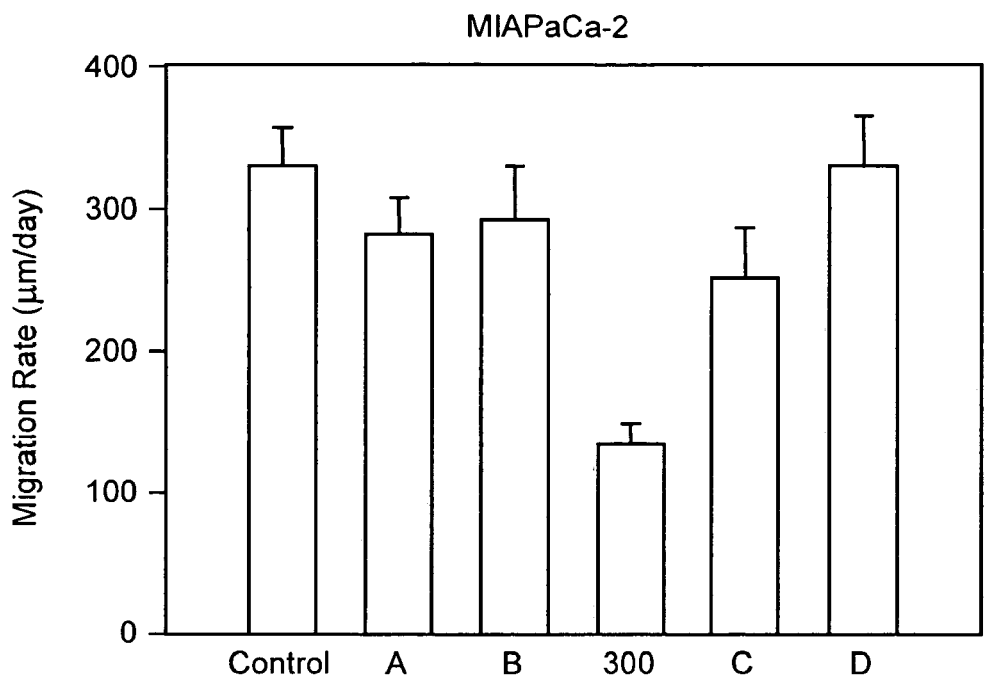
FIG. 18 is a bar graph illustrating cell migration rate for an untreated sample of pancreatic cancer cells and various treated samples of pancreatic cancer cells.

FIG. 18 is a bar graph illustrating cell migration rate, in units of μm/day, for an untreated sample of pancreatic cancer cells and various treated samples of pancreatic cancer cells. The pancreatic cancer cell line is MiaPaCa-2. The control sample is the untreated cancer cells. Sample 300 was treated with a chemical having a formula of: 1-(4-chloro-benzoyl)-2-(3,4-dimethoxy-phenyl)-1,2-dihydro-3aH-pyrrolo[1,2-a]quinoline-3,3-dicarbonitrile. Samples A, B, C, and D were treated with chemicals having substantially different formulas than the chemical used to treat sample 300. As shown in FIG. 18, the pancreatic cancer cells treated with 1-(4-chloro-benzoyl)-2-(3,4-dimethoxy-phenyl)-1,2-dihydro-3aH-pyrrolo[1,2-a]quinoline-3,3-dicarbonitrile show markedly reduced migration in comparison to the untreated control sample and the other treated samples. Therefore, 1-(4-chloro-benzoyl)-2-(3,4-dimethoxy-phenyl)-1,2-dihydro-3aH-pyrrolo[1,2-a]quinoline-3,3-dicarbonitrile has been identified as a cell migration inhibiting chemical.

Example 13

Figure 19:
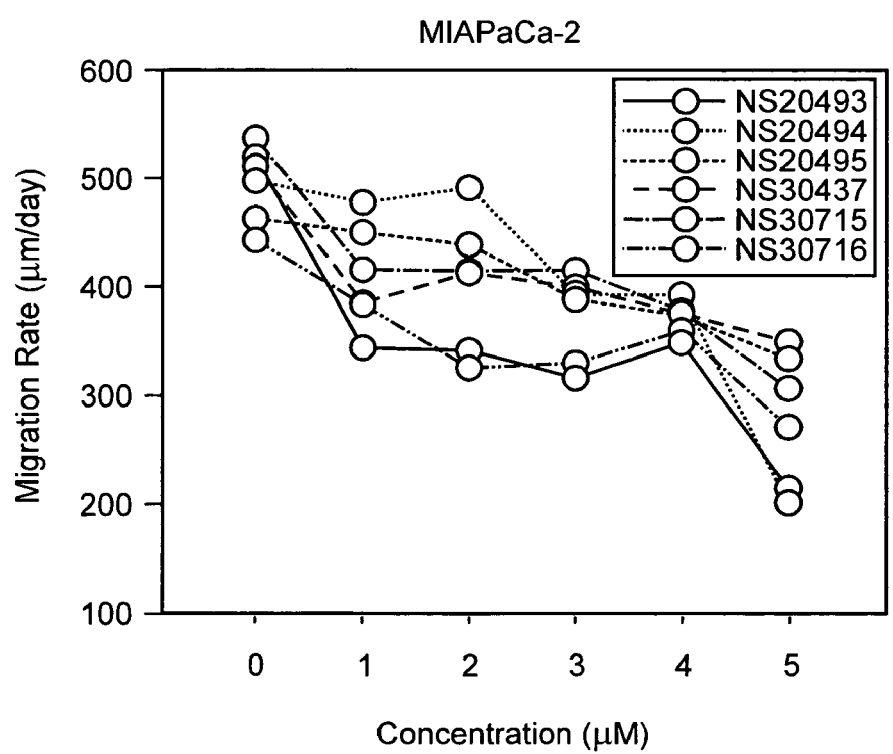
FIG. 19 is a plot illustrating cell migration rate of pancreatic cancer cells as a function of concentration of several different chemicals.

Dose Response Curve of Pancreatic Cancer Cells to a Cell Migration Inhibitor FIG. 19 is a plot illustrating cell migration rate, in units of μm/day, as a function of concentration of several different chemicals, in units of μM. NS20494 indicates the cell migration rate of pancreatic cells treated with 1-(4-chloro-benzoyl)-2-(3,4-dimethoxy-phenyl)-1,2-dihydro-3aH-pyrrolo [1,2-a]quinoline-3,3-dicarbonitrile. This chemical was selected from a plurality of chemicals from a library because pancreatic cancer cells treated with the chemical had a lower cell migration rate than untreated cancer cells and several other samples of cancer cells treated with other chemicals as described above.

In addition, chemicals having a formula analogous to this chemical were selected based on the cell migration inhibition of 1-(4-chloro-benzoyl)-2-(3,4-dimethoxy-phenyl)-1,2-dihydro-3aH-pyrrolo[1,2-a]quinoline-3,3-dicarbonitrile. NS20493 indicates the cell migration rate of pancreatic cells treated with 2-{[1-(4-chloro-benzoyl)-2-phenyl-1,2,3,3a-tetrahydro-pyrrolo[1,2-a]quinoline-3-yl]-cyclopropyl-methylene}-malononitrile. NS20495 indicates the cell migration rate of pancreatic cells treated with 1-benzoyl-2-(3,4-dimethoxy-phenyl)-1,2-dihydro-3aH-pyrrole[1,2-a]quinoline-3,3-carbonitrile. NS30437 indicates the cell migration rate of pancreatic cells treated with 2-benzo[1,3]dioxol-5-yl-1-cycloprpanecarbonyl-1,2-dihydro-3aH-pyrrolo[1,2-a] quinoline-3,3-dicarbonitrile. NS30715 indicates the cell migration rate of pancreatic cells treated with 1-(4-chloro-benzoyl)-2-(4-fluoro-phenyl)-1,2-dihydro-3aH-pyrrolo[1,2-a]quinoline-3,3-dicarbonitrile. NS30716 indicates the cell migration rate of pancreatic cells treated with 1-(4-chloro-benzoyl)-2-(4-methoxy-phenyl)-1,2-dihydro-3aH-pyrrolo [1,2-a]quinoline-3,3-dicarbonitrile.

Several samples of pancreatic cancer cells were treated with various concentrations of each chemical. The pancreatic cancer cell line is MiaPaCa-2. The concentration of the chemicals was varied from 0 μM to 5 μM. The cell migration rate of each sample of the cancer cells was measured. As shown in FIG. 19, the cell migration rate decreased from about 500 μm/day at a concentration of 0.000 μM for each of the chemicals to less than 400 μm/day at a concentration of 5.00 μM for each of the chemicals, and to about 200 μm/day at a concentration of 5.00 μM for some of the chemicals. Therefore, these chemicals were identified as pancreatic cancer cell migration inhibiting chemicals.

Example 14

Angiogenesis Inhibition 0

Figure 20:
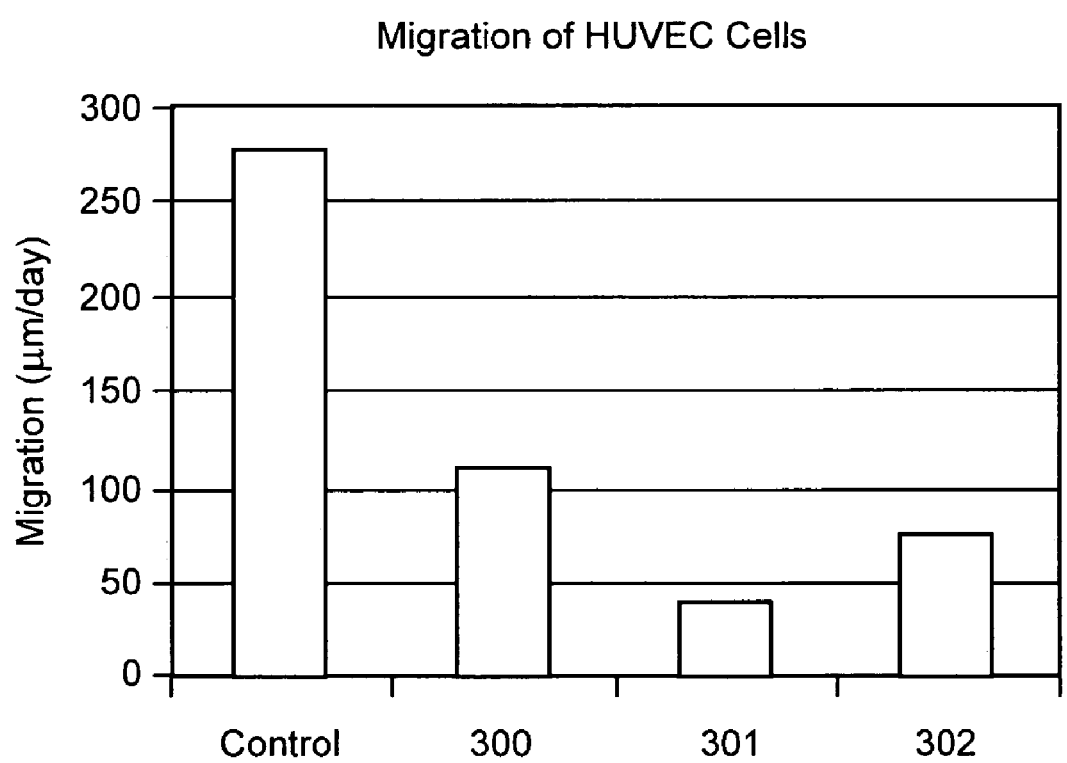
FIG. 20 is a bar graph illustrating cell migration rate for an untreated sample of HUVEC cells and treated samples of HUVEC cells.

FIG. 20 is a bar graph illustrating cell migration rate, in units of μm/day for an untreated sample of HUVEC cells and treated samples of HUVEC cells. The control sample is the untreated cancer cells. The treated samples were treated with three different chemicals selected from a library of chemicals. The treated samples are labeled 300, 301, and 302. The sample labeled 300 was treated with 1-(4-chloro-benzoyl)-2-(3,4-dimethoxy-phenyl)-1,2-dihydro-3aH-pyrrolo[1,2-a] quinoline-3,3-dicarbonitrile. The sample labeled 301 was treated with N-(3-cyano-4,5,6,7-tetrahydro-benzo[b] thiophen-2-yl)-3-iodo-benzamide. The sample labeled 302 was treated with [5-(2,3-dihydro-benzo[1,4]dioxin-6-yl)-4H-[1,3,4]thiadiazin-2-yl]-phenyl-amine. As shown in FIG. 20, the HUVEC cells treated with each of the above chemicals show markedly reduced migration in comparison to the untreated control sample. Therefore, 1-(4-chloro-benzoyl)-2-(3,4-dimethoxy-phenyl)-1,2-dihydro-3aH-pyrrolo[1,2-a] quinoline-3,3-dicarbonitrile, N-(3-cyano-4,5,6,7-tetrahydrobenzo[b]thiophen-2-yl)-3-iodo-benzamide, and [5-(2,3-dihydro-benzo[1,4]dioxin-6-yl)-4H-[1,3,4]thiadiazin-2-yl]-phenyl-amine have been identified as angiogenesis inhibiting chemicals.

Example 15

Effects of Cell Migration Inhibitors of Normal Fibroblasts

Figure 21:
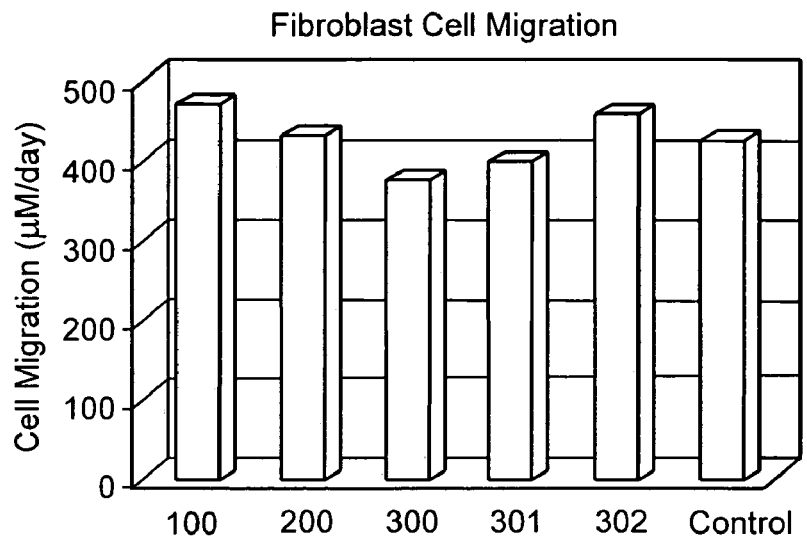
FIG. 21 is a bar graph illustrating cell migration rate of normal fibroblasts for cells treated with various cell migration inhibitors and a control sample of untreated cells.

FIG. 21 is a bar graph illustrating cell migration rate of normal fibroblasts, in units of mM/day, for cells treated with various cell migration inhibitors and a control sample of untreated cells. The chemical labeled 100 is 4'-propyl-bicyclohexyl-4-carboxylic acid. The chemical labeled 200 is 4-methyl-3-nitro-benzoic acid. The chemical labeled 300 is 1-(4-chloro-benzoyl)-2-(3,4-dimethoxy-phenyl)-1,2-dihydro-3aH-pyrrolo[1,2-a]quinoline-3,3-dicarbonitrile. The chemical labeled 301 is N-(3-cyano-4,5,6,7-tetrahydrobenzo[b]thiophen-2-yl)-3-iodo-benzamide. The chemical labeled 302 is [5-(2,3-dihydro-benzo[1,4]dioxin-6-yl)-4H-[1,3,4]thiadiazin-2-yl]-phenyl-amine. As shown in FIG. 21, each of the cell migration inhibitors has essentially no effect on the cell migration of normal fibroblasts.

Example 16

Synergy of a Cell Migration Inhibitor and a Chemotherapeutic Agent

Figure 22:
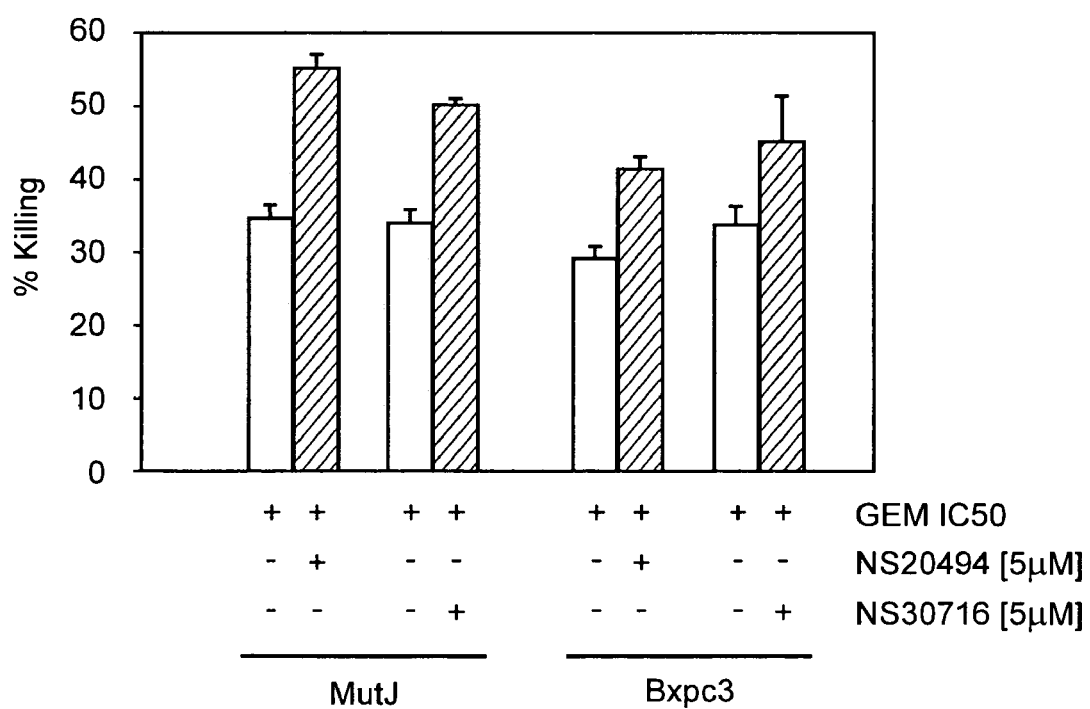
FIG. 22 is a bar graph illustrating % killing of different cancer cells as a function of a chemotherapeutic agent alone or in combination with different cell migration inhibitors.

FIG. 22 is a bar graph illustrating % killing of different cancer cells, in units of % dead cells, as a function of a chemotherapeutic agent alone or in combination with different cell migration inhibitors. The pancreatic cancer cell lines are MutJ and Bxpc3. Such cancer cell lines may be obtained from cell collections such as American Type Culture Collection, Manassas, Va., European Collection of Cell Cultures (CAMR Centre for Applied Microbiology and Research), Salisbury, Wiltshire, United Kingdom, and Interlab Cell Line Collection (Instituto Nazionale per la Ricerca sul Cancro), Genova, Italy. The chemotherapeutic agent is gemcytabine, which is commercially available as Gemzar® from Eli Lilly and Company, Indianapolis, Ind. The cell migration inhibitors are 1-(4-chloro-benzoyl)-2-(3,4-dimethoxy-phenyl)-1, 2-dihydro-3aH-pyrrolo[1,2-a]quinoline-3,3-dicarbonitrile, which is labeled as NS20494, and 1-(4-chloro-benzoyl)-2-(4-methoxy-phenyl)-1,2-dihydro-3aH-pyrrolo[1,2-a]quinoline-3,3-dicarbonitrile, which is labeled as NS30716. The pluses and minuses below the graph indicate the chemicals that were used to treat the different samples. For example, from left to right on the x-axis, the first sample of MutJ cells was treated with gemcytabine only, and the second sample of MutJ cells was treated with a combination of gemcytabine and NS20494. The concentration of the cell migration inhibitor in the cell migration inhibitor-containing treatments was 5 μM.

The data shown in FIG. 22 was generated by an MTS Assay Method. This assay is a colorimetric method for determining the number of viable cells in proliferation or chemosenstivity assays. Such an assay is commercially available as CellTiter 96® AQ$_{ueous}$ Non-Radioactive Cell Proliferation Assay from Promega Corporation, Madison, Wis. The assay includes a tetrazolium compound, 3-(4,5-dimethylthiazol-2-yl)-5-(3-carboxymethoxyphenyl)-2-(4-sulfophenyl)-2H-tetrazolium, inner salt (MTS), and an electron coupling reagent, phenazine methosulfate (PMS). MTS is bioreduced by cells into a formazan product that is soluble in tissue culture medium. The absorbance of the fomazan at 490 nm can be measured directly from 96 well assay plate without additional processing and is directly proportional to the number of living cells in culture.

The desired number of cells were deposited on a 96-well flat bottom microtiter plate in 0.10 ml of a solution containing Roswell Park Memorial Institute (RPMI) medium with 5% fetal calf serum (FCM), 1% L-glutamine (a non-essential amino acid), and 1% Penicillin-Streptomycin (Pen-Strep). The plate is commercially available as Falcon™ 353072 BD Falcon Clear 96-well Microtest Plate from BD Biosciences (Becton, Dickinson and Company), Franklin Lakes, N.J. The plate has a flat bottom and a low-evaporation lid, a 0.32 $cm^2$ growth area, and a 370 µl well volume. The plate is made of a vacuum-gas plasma tissue-culture treated polystyrene for uniform surface chemistry. A scincillator counter was used to count cells. For example, the cells were deposited and counted such that each sample included about 8226 cells (8226/S) or about 4000 cells per well, about 8226 cells per optic density times 40 (8226/DO×40) or about 5000 cells per well. 0.01 ml of 10× drug dilution was added to each well, where 10× indicates that the stock solution was diluted by a factor of 10 from its original 100× stock solution. 0.01 ml media was also added to control wells. The plate was incubated for 4 days in a 37° C., 5% $CO_2$, humidified incubator.

MTS is commercially available as CellTiter 96® $AQ_{ueous}$ MTS Powder from Promega. The MTS was dissolved in phosphate-buffered saline (PBS) at a concentration of 2 mg/ml and stored at −20° C. PMS is commercially available from Sigma-Aldrich Corporation, St. Louis, Mo. A solution of PMS in PBS at a concentration of 0.92 mg/ml was prepared and stored at −20° C. The MTS and PMS were thawed in a 37° C. water bath for approximately 10 minutes before use. MTS and PMS were mixed in a ratio of 20:1 (i.e., 2 ml of MTS and 100 µl of PMS) just before addition to the wells. 20 µl of the MTS/PMS mixture was added to each well. The plate was incubated for 3 to 4 hours in a 37° C., 5% $CO_2$, humidified incubator. The absorbance at 490 nm was recorded using a spectrophotometric microplate reader. In addition, if the absorbance is to be recorded at a later time, 25 µl of 10% sodium dodecyl sulfate (SDS) may be added to each well to stop the reaction. The SDS-treated plates may be protected from light in a humidified chamber at room temperature for up to 18 hours. The absorbance may be recorded as described above.

As shown in FIG. 22, the combination of gemcytabine and NS20494 or NS30716 exhibits higher killing percentages than gemcytabine alone for each of the cells lines. Therefore, the combination of gemcytabine and NS20494 or NS30716 exhibits synergistic killing of pancreatic cancer cells. As such, a pharmaceutical composition of the combination of gemcytabine and NS20494 or NS30716 may have greater efficacy than gemcytabine alone.

It will be appreciated to those skilled in the art having the benefit of this disclosure that this invention is believed to provide compositions that alter cell migration and methods for treating cancer by inhibiting cell migration. Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A pharmaceutical composition, comprising a cell migration inhibitor and a chemotherapeutic agent, wherein the inhibitor is 1-(4-chloro-benzoyl)-2-(3,4-dimethoxy-phenyl)-1,2-dihydro-3aH-pyrrolo[1,2-a]quinoline-3,3-dicarbonitrile.

2. The composition of claim 1, wherein the chemotherapeutic agent is selected from the group consisting of an alkylating agent, an antitumor antibiotic, an antimetabolite, an antimicrotubule agent, a spindle-tubule inhibitor, a topoisomerase inhibitor, a hormonal agent, a biological agent, and a granulocyte-colony stimulating factor.

3. A method for treating an individual having cancer, comprising administering a cell migration inhibitor and a chemotherapeutic agent to the individual, wherein the inhibitor is 1-(4-chloro-benzoyl)-2-(3,4-dimethoxy-phenyl)-1,2-dihydro-3aH-pyrrolo[1,2-a]quinoline-3,3-dicarbonitrile.

4. A pharmaceutical composition, comprising a cell migration inhibitor and a chemotherapeutic agent, wherein the cell migration inhibitor is 1-(4-chloro-benzoyl)-2-(3,4-dimethoxy-phenyl)-1,2-dihydro-3aH-pyrrolo[1,2-a]quinoline-3,3-dicarbonitrile, wherein the chemotherapeutic agent is gemcytabine, and wherein the composition exhibits synergistic killing of pancreatic cancer cells.

5. A method for treating an individual having pancreatic cancer, comprising administering a cell migration inhibitor and a chemotherapeutic agent to the individual, wherein the cell migration inhibitor is 1-(4-chloro-benzoyl)-2-(3,4-dimethoxy-phenyl)-1,2-dihydro-3aH-pyrrolo[1,2-a]quinoline-3,3-dicarbonitrile, wherein the chemotherapeutic agent is gemcytabine.

6. The composition of claim 1, wherein the chemotherapeutic agent is 1,3-bis(2-chloroethyl)-1-nitrosourea.

7. The composition of claim 1, wherein the chemotherapeutic agent is paclitaxel.

8. The composition of claim 1, wherein the chemotherapeutic agent is fluorouracil.

9. The composition of claim 1, wherein the chemotherapeutic agent is cytarabine.

10. The method of claim 3, wherein the chemotherapeutic agent is selected from the group consisting of alkylating agent, an antitumor antibiotic, an antimetabolite, an antimicrotubule agent, a spindle-tubule inhibitor, a topoisomerase inhibitor, a hormonal agent, a biological agent, and a granulocyte-colony stimulating factor.

11. The composition of claim 1, wherein the chemotherapeutic agent is gemcytabine.

* * * * *